US010045133B2

(12) United States Patent
Bauman et al.

(10) Patent No.: US 10,045,133 B2
(45) Date of Patent: *Aug. 7, 2018

(54) VARIABLE SOUND ATTENUATOR WITH HEARING AID

(71) Applicants: Natan Bauman, Hamden, CT (US); Ralph T. Campagna, Danielson, CT (US)

(72) Inventors: Natan Bauman, Hamden, CT (US); Ralph T. Campagna, Danielson, CT (US)

(*) Notice: Subject to any disclaimer, the term of this patent is extended or adjusted under 35 U.S.C. 154(b) by 3 days.

This patent is subject to a terminal disclaimer.

(21) Appl. No.: 15/148,809

(22) Filed: May 6, 2016

(65) Prior Publication Data

US 2016/0255449 A1 Sep. 1, 2016
US 2018/0139549 A9 May 17, 2018

Related U.S. Application Data

(63) Continuation-in-part of application No. 14/212,409, filed on Mar. 14, 2014, now Pat. No. 9,333,116, and
(Continued)

(51) Int. Cl.
*H04R 3/00* (2006.01)
*H04R 25/00* (2006.01)
(Continued)

(52) U.S. Cl.
CPC .............. *H04R 25/75* (2013.01); *A61F 11/08* (2013.01); *G10K 11/16* (2013.01); *H04R 25/402* (2013.01);
(Continued)

(58) Field of Classification Search
CPC ........ G02B 27/0172; G02B 2027/0132; G02B 2027/0178; G02B 2027/014;
(Continued)

(56) References Cited

U.S. PATENT DOCUMENTS 2,850,012 A   9/1958  Becker
2,876,767 A   3/1959  Wasserman
(Continued)

FOREIGN PATENT DOCUMENTS

EP   0077688 A1   4/1983
EP   1326479 B1   7/2003

OTHER PUBLICATIONS

Schmid, "Aging Nation Faces Growing Hearing Loss", Copyright 2007—Assosiated Press.
(Continued)

*Primary Examiner* — Muhammad N Edun
(74) *Attorney, Agent, or Firm* — St Onge Steward Johnston and Reens LLC

(57) ABSTRACT

A device combining a variable sound attenuator with a hearing device, (such as a hearing aid or tinnitus device) that allows a user to adjust the amount of attenuation of environmental sound in a variable, continuous fashion or in a discrete controlled fashion from zero attenuation to maximum attenuation without removing the device from the ear. The attenuator includes a housing having a passageway, the passageway allowing for sound to pass through the housing and a variable control, the variable control able to control the size of the passageway through the housing and the device including a second passageway for transmitting amplified sound from the hearing device into the ear of the wearer.

21 Claims, 15 Drawing Sheets

Related U.S. Application Data a continuation-in-part of application No. 14/448,732, filed on Jul. 31, 2014, now Pat. No. 9,521,480.

(60) Provisional application No. 61/790,243, filed on Mar. 15, 2013, provisional application No. 61/860,534, filed on Jul. 31, 2013.

(51) Int. Cl.
 *A61F 11/08* (2006.01)
 *G10K 11/16* (2006.01)
 *H03G 3/04* (2006.01)

(52) U.S. Cl.
 CPC .......... *A61F 2011/085* (2013.01); *H03G 3/04* (2013.01); *H04R 2225/61* (2013.01); *H04R 2430/01* (2013.01)

(58) Field of Classification Search
 CPC .......... G02B 2027/0123; G02B 27/283; G02B 27/0176; G02B 2027/015
 See application file for complete search history.

(56) References Cited

U.S. PATENT DOCUMENTS

| | | | |
|---|---|---|---|
| 3,110,356 A | 11/1963 | Mendelson | |
| 3,505,999 A | 4/1970 | Harvey et al. | |
| 3,602,654 A | 8/1971 | Victoreen | |
| 4,006,796 A | 2/1977 | Coehorst | |
| 4,029,083 A | 6/1977 | Baylor | |
| 4,060,080 A | 11/1977 | Akiyama | |
| 4,232,084 A | 11/1980 | Tate | |
| 4,556,122 A | 12/1985 | Goode | |
| 4,834,211 A | 5/1989 | Bibby et al. | |
| 4,896,679 A | 1/1990 | St. Pierre | |
| 4,913,165 A | 4/1990 | Fishgoyt | |
| 5,084,224 A | 1/1992 | Watters | |
| 5,131,411 A | 7/1992 | Casali et al. | |
| 5,259,033 A | 11/1993 | Goodings et al. | |
| 5,333,622 A | 8/1994 | Casali et al. | |
| 5,600,729 A | 2/1997 | Darlington et al. | |
| 5,651,071 A | 7/1997 | Lindemann et al. | |
| 5,675,658 A | 10/1997 | Brittain | |
| 6,082,485 A | 7/2000 | Smith | |
| 6,148,821 A | 11/2000 | Falco | |
| 6,286,622 B1 | 9/2001 | Tiemann | |
| 6,368,288 B2 | 4/2002 | Stone | |
| 6,368,289 B2 | 4/2002 | Stone | |
| 6,440,102 B1 | 8/2002 | Arenberg et al. | |
| 7,171,371 B2 | 1/2007 | Goldstein | |
| 7,424,123 B2 | 9/2008 | Shennib et al. | |
| 7,756,281 B2 | 7/2010 | Goldstein et al. | |
| 7,779,844 B2 | 8/2010 | Purcell | |
| 7,817,803 B2 | 10/2010 | Goldstein | |
| 7,822,219 B2 | 10/2010 | Baker et al. | |
| 7,837,008 B1 | 11/2010 | Lane et al. | |
| 7,882,928 B2 | 2/2011 | McMahon et al. | |
| 7,886,745 B2 | 2/2011 | Purcell et al. | |
| 7,913,696 B2 | 3/2011 | Purcell et al. | |
| 8,018,328 B2 | 9/2011 | Goldstein et al. | |
| 8,047,207 B2 | 11/2011 | Perez et al. | |
| 8,081,780 B2 | 12/2011 | Goldstein et al. | |
| 8,111,839 B2 | 2/2012 | Goldstein et al. | |
| 8,118,031 B2 | 2/2012 | Seville | |
| 8,142,870 B2 | 3/2012 | Keady | |
| 8,150,043 B2 | 4/2012 | Goldstein et al. | |
| 8,150,044 B2 | 4/2012 | Goldstein et al. | |
| 8,155,361 B2 | 4/2012 | Schindler | |
| 8,170,228 B2 | 5/2012 | Goldstein et al. | |
| 8,194,864 B2 | 6/2012 | Goldstein et al. | |
| 8,194,865 B2 | 6/2012 | Goldstein et al. | |
| 8,199,919 B2 | 6/2012 | Goldstein et al. | |
| 8,208,644 B2 | 6/2012 | Goldstein et al. | |
| 8,208,652 B2 | 6/2012 | Keady | |
| 8,213,629 B2 | 7/2012 | Goldstein et al. | |
| 8,213,649 B2 | 7/2012 | Goldstein et al. | |
| 8,221,860 B2 | 7/2012 | Keady | |
| 8,221,861 B2 | 7/2012 | Keady | |
| 8,229,128 B2 | 7/2012 | Keady | |
| 8,251,925 B2 | 8/2012 | Keady et al. | |
| 8,311,228 B2 | 11/2012 | Goldstein et al. | |
| 8,312,960 B2 | 11/2012 | Keady | |
| 8,315,400 B2 | 11/2012 | Goldstein et al. | |
| 8,319,620 B2 | 11/2012 | Usher et al. | |
| 8,326,628 B2 | 12/2012 | Goldstein et al. | |
| 8,326,635 B2 | 12/2012 | Usher et al. | |
| 8,340,333 B2 | 12/2012 | Wilson | |
| 8,437,492 B2 | 5/2013 | Goldstein et al. | |
| 8,447,031 B2 | 5/2013 | Usher et al. | |
| 8,550,206 B2 | 10/2013 | Keady et al. | |
| 9,197,970 B2 | 11/2015 | Zhang et al. | |
| 9,521,480 B2 * | 12/2016 | Bauman | H04R 1/1083 |
| 2002/0143242 A1 | 10/2002 | Nemirovski | |
| 2006/0042640 A1 * | 3/2006 | Haussmann | A61F 11/08 128/864 |
| 2006/0042868 A1 | 3/2006 | Berg et al. | |
| 2007/0270988 A1 | 11/2007 | Goldstein et al. | |
| 2008/0015463 A1 | 1/2008 | Goldstein | |
| 2008/0031475 A1 | 2/2008 | Goldstein | |
| 2008/0037797 A1 | 2/2008 | Goldstein et al. | |
| 2008/0046246 A1 | 2/2008 | Goldstein et al. | |
| 2008/0130906 A1 | 6/2008 | Goldstein et al. | |
| 2008/0137873 A1 | 6/2008 | Goldstein | |
| 2008/0144840 A1 | 6/2008 | Goldstein et al. | |
| 2008/0144841 A1 | 6/2008 | Goldstein et al. | |
| 2008/0144842 A1 | 6/2008 | Goldstein et al. | |
| 2008/0176289 A1 | 7/2008 | Zeng et al. | |
| 2008/0178088 A1 | 7/2008 | Goldstein et al. | |
| 2008/0181419 A1 | 7/2008 | Goldstein et al. | |
| 2008/0181442 A1 | 7/2008 | Goldstein et al. | |
| 2008/0205660 A1 | 8/2008 | Goldstein | |
| 2008/0212787 A1 | 9/2008 | Goldstein et al. | |
| 2008/0219456 A1 | 9/2008 | Goldstein et al. | |
| 2008/0219486 A1 | 9/2008 | Goldstein et al. | |
| 2008/0240458 A1 | 10/2008 | Goldstein et al. | |
| 2008/0253583 A1 | 10/2008 | Goldstein et al. | |
| 2008/0267416 A1 | 10/2008 | Goldstein et al. | |
| 2008/0269636 A1 | 10/2008 | Burrows et al. | |
| 2008/0299339 A1 | 12/2008 | Keady | |
| 2008/0311324 A1 | 12/2008 | Keady | |
| 2009/0016541 A1 | 1/2009 | Goldstein et al. | |
| 2009/0016542 A1 | 1/2009 | Goldstein et al. | |
| 2009/0022294 A1 | 1/2009 | Goldstein et al. | |
| 2009/0022353 A1 | 1/2009 | Goldstein et al. | |
| 2009/0028356 A1 | 1/2009 | Ambrose et al. | |
| 2009/0034748 A1 | 2/2009 | Sibbald | |
| 2009/0034765 A1 | 2/2009 | Boillot et al. | |
| 2009/0067661 A1 | 3/2009 | Keady et al. | |
| 2009/0071486 A1 | 3/2009 | Perez et al. | |
| 2009/0071487 A1 | 3/2009 | Keady | |
| 2009/0130423 A1 | 5/2009 | Keady | |
| 2009/0146799 A1 | 6/2009 | Goldstein et al. | |
| 2009/0147966 A1 | 6/2009 | McIntosh et al. | |
| 2009/0154748 A1 | 6/2009 | Baker et al. | |
| 2009/0155518 A1 | 6/2009 | Keady | |
| 2009/0192407 A1 | 7/2009 | Keady et al. | |
| 2009/0214072 A1 | 8/2009 | Staab et al. | |
| 2009/0220096 A1 | 9/2009 | Usher et al. | |
| 2009/0238374 A1 | 9/2009 | Keady | |
| 2009/0238386 A1 | 9/2009 | Usher et al. | |
| 2009/0240497 A1 | 9/2009 | Usher et al. | |
| 2009/0245530 A1 | 10/2009 | Keady | |
| 2009/0264161 A1 | 10/2009 | Usher et al. | |
| 2009/0290721 A1 | 11/2009 | Goldstein et al. | |
| 2010/0002897 A1 | 1/2010 | Keady | |
| 2010/0012420 A1 | 1/2010 | Keady | |
| 2010/0033313 A1 | 2/2010 | Keady et al. | |
| 2010/0071707 A1 | 3/2010 | Wohl | |
| 2010/0074451 A1 | 3/2010 | Usher et al. | |
| 2010/0076793 A1 | 3/2010 | Goldstein et al. | |
| 2010/0135502 A1 | 6/2010 | Keady et al. | |
| 2010/0142715 A1 | 6/2010 | Goldstein et al. | |
| 2010/0142725 A1 | 6/2010 | Goldstein et al. | |

(56) References Cited

U.S. PATENT DOCUMENTS

| | | |
|---|---|---|
| 2010/0177918 A1 | 7/2010 | Keady et al. |
| 2010/0241256 A1 | 9/2010 | Goldstein et al. |
| 2010/0322454 A1 | 12/2010 | Ambrose et al. |
| 2011/0079227 A1 | 4/2011 | Turcot et al. |
| 2011/0085689 A1 | 4/2011 | Keady |
| 2011/0115626 A1 | 5/2011 | Goldstein et al. |
| 2011/0158420 A1 | 6/2011 | Hannah |
| 2011/0206214 A1 | 8/2011 | Christoph et al. |
| 2011/0228963 A1 | 9/2011 | Goldstein et al. |
| 2011/0235843 A1 | 9/2011 | Keady et al. |
| 2011/0311079 A1 | 12/2011 | Keady |
| 2012/0101514 A1 | 4/2012 | Keady et al. |
| 2012/0103346 A1 | 5/2012 | Keady |
| 2012/0123573 A1 | 5/2012 | Goldstein et al. |
| 2012/0177209 A1 | 7/2012 | Goldstein et al. |
| 2012/0177210 A1 | 7/2012 | Goldstein et al. |
| 2012/0288104 A1 | 11/2012 | Goldstein et al. |
| 2012/0318605 A1 | 12/2012 | Brown |
| 2013/0035608 A1 | 2/2013 | Goldstein et al. |
| 2013/0039518 A1 | 2/2013 | Goldstein et al. |
| 2013/0098706 A1 | 4/2013 | Keady |
| 2013/0123919 A1 | 5/2013 | Goldstein et al. |

OTHER PUBLICATIONS

Passchier-Vermeer, et al., "Noise Exposure and Public Health", Environ Health Persoect., Mar. 2000, pp. 123-131 (abstract only).
Rosenhall, et al., "Presbycusis and Noise-Induced Hearing Loss"; Ear Hear, Aug. 1990, 1 page abstract.

* cited by examiner

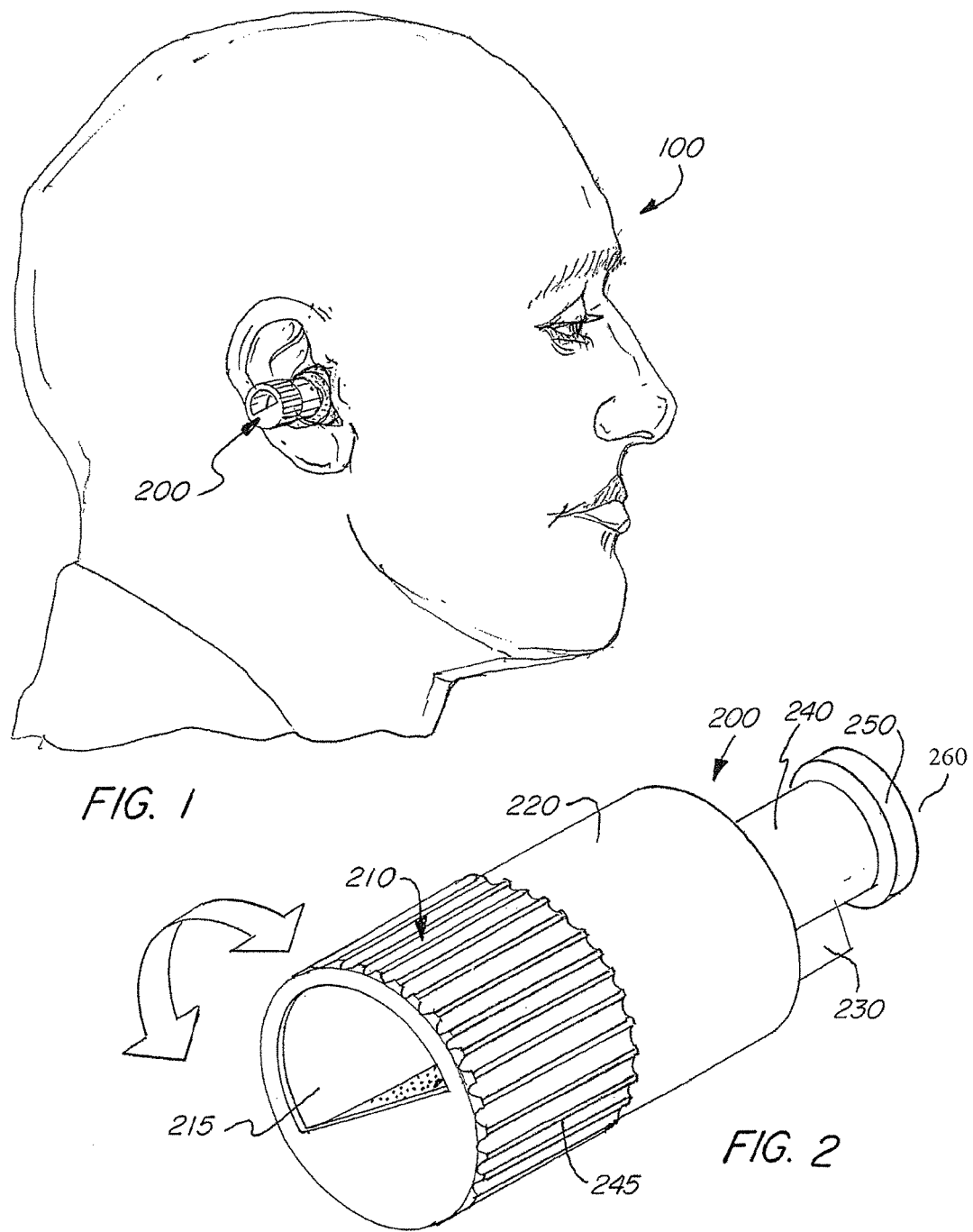

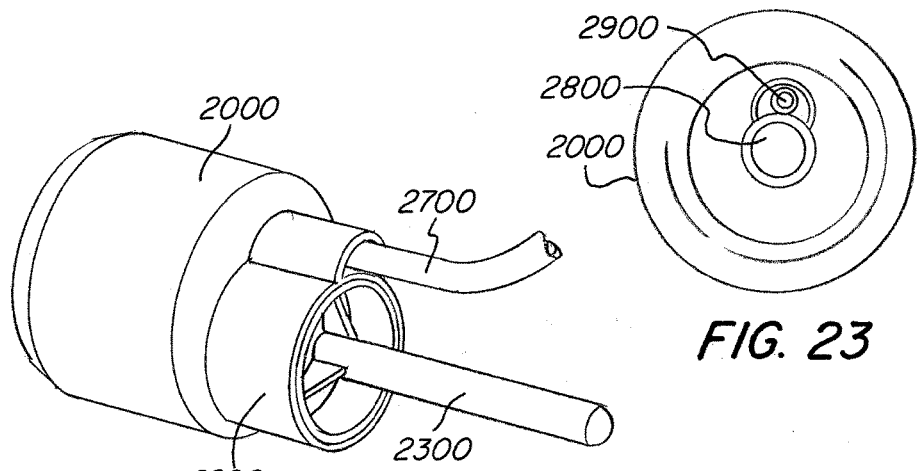
FIG. 22
FIG. 23
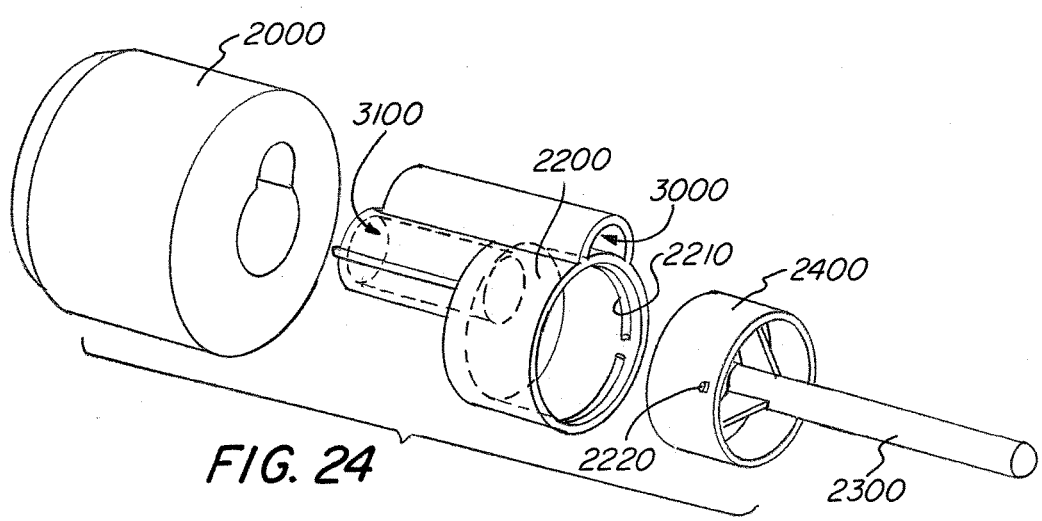
FIG. 24
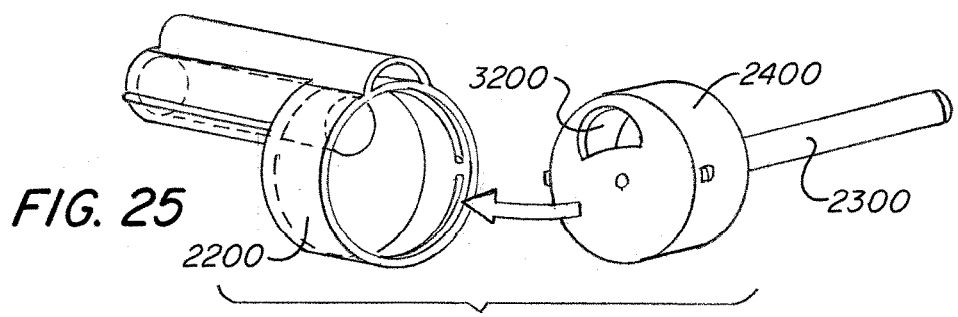
FIG. 25

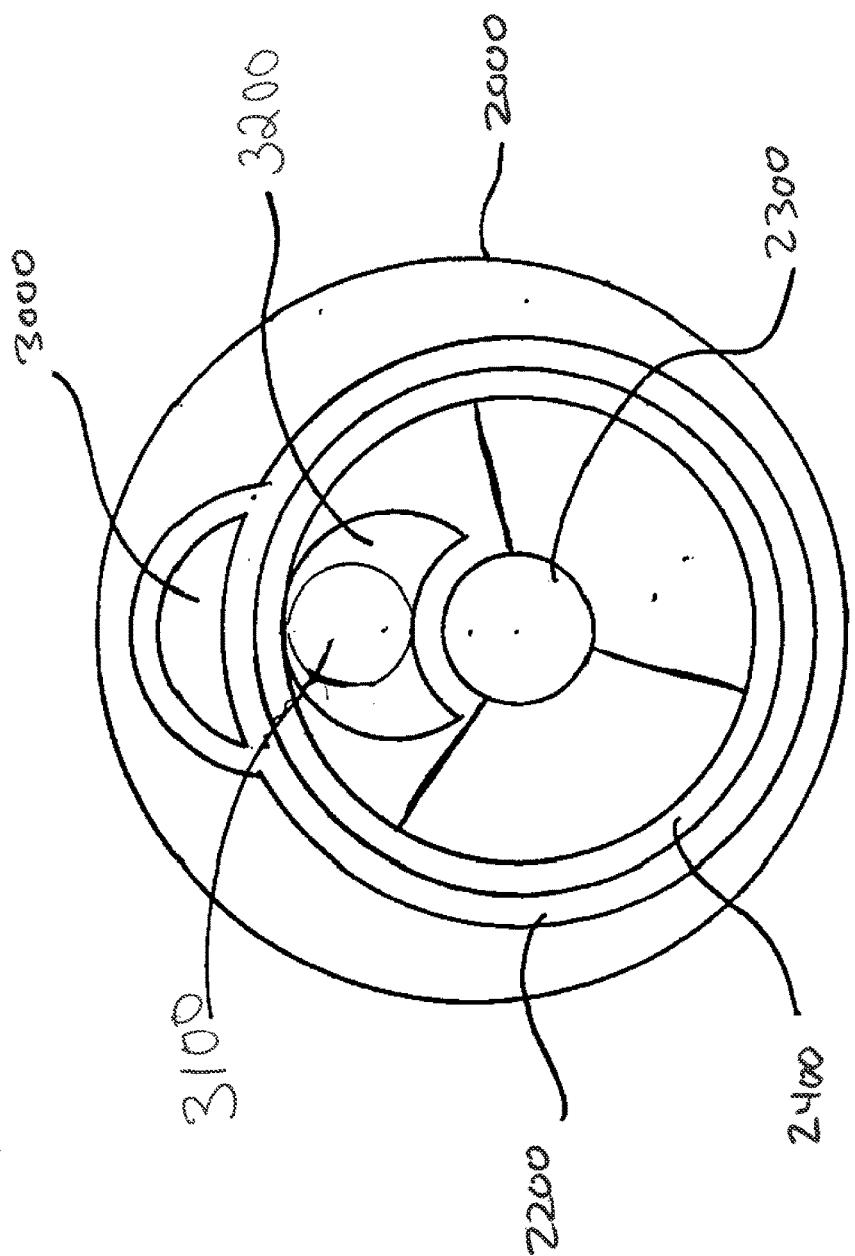

VARIABLE SOUND ATTENUATOR WITH HEARING AID

FIELD OF THE INVENTION

A device including an ear worn attenuator and hearing aid/tinnitus device that allows a user to adjust the amount of attenuation of environmental sound in a variable, continuous and or discrete fashion from zero attenuation to maximum attenuation without removing the device from the ear.

BACKGROUND OF THE INVENTION

According to Occupational Safety & Health Administration (OSHA), about 30 million people in the United States are exposed to hazardous occupational noise every year (Internet, United State Department of Labor, OSHA, Safety and Health Topics, 2014). Noise-related hearing loss has been listed as one of the most widespread occupational health concerns in the United States for more than 25 years. Thousands of workers every year suffer from preventable hearing loss due to high workplace noise levels. Rosenhall U, Pedersen K, Svanborg A (1990). "Presbycusis and noise-induced hearing loss". Ear Hear 11 (4): 257-63; Schmid, R E (Feb. 18, 2007). "Aging nation faces growing hearing loss". CBS News. Retrieved Feb. 18, 2007; Senate Public Works Committee, Noise Pollution and Abatement Act of 1972, S. Rep. No. 1160, 92nd Cong. 2nd session.

According to Wikipedia; "Noise health effects are the health consequences of elevated sound levels. Elevated noise levels at workplace or other noise can cause hearing impairment, hypertension, ischemic heart disease, annoyance, and sleep disturbance. Changes in the immune system and birth defects have been attributed to noise exposure". Passchier-Vermeer W, Passchier W F (2000). "Noise exposure and public health". Environ. Health Perspect. 108 Suppl 1: 123-31.

Noise exposure also has been known to induce tinnitus, hypertension, vasoconstriction, and other cardiovascular adverse effects. Health Effects and Controls". University of California, Berkeley. Archived from the original on Sep. 25, 2007. Increased levels of noise have been also found to be responsible for creating stress, increase workplace accident rates, and stimulate aggression and other anti-social behaviors.

A comprehensive report on effects of noise has been published in 1991 and it is a summary of the "Administrative Conference of the United States Noise and Its Effects" by Dr. Alice H. Suter, Conference Consultan, (November 1991).

A problem exists whereby there is a need to provide an ear attenuator which allows a user to change the amount of sound protection quickly and according to the amount of noise in the environment and also according to the need of being able to maintain communication. For example, at a construction site, at one moment the construction worker needs to be protected from very loud construction equipment and at a moment later the same construction worker may need to be able to recognize warning sounds or instructions given by a supervisor or may need to be able to recognize a warning sound from a piece of equipment.

In another example, a hunter needs to hear the faint sounds of the hunting animal but yet at the time of rifle fire he needs to protect his hearing. On a battle field soldiers need to protect their hearing from very loud explosions but also they need to hear commands as well as very faint sounds of their foes. In yet another example, a musician who wants to protect his hearing from the loud sounds of an orchestra may also need to hear instructions given by the conductor.

In a report from Stakeholder Meeting on Preventing Occupational Hearing Loss Washington, D.C. Nov. 3, 2011, Meeting Summary Report, quote "Hearing protection devices can interfere with speech and alarm detection for workers. This is especially true for many older workers, who already have noise-induced hearing loss. Hearing protectors often attenuate higher frequencies, which is the range in which speech and information is often conveyed. Making hearing protection devices compulsory puts some workers in danger. In fact, many workers find ways to sabotage hearing protection in order to communicate."

One consequence of improper attenuation in hearing protection device (HPD) is that a user may reject the hearing protection (as cited above) if it compromises his/her hearing to the extent that sounds no longer appear natural, signals cannot be detected or localized, and/or speech is not intelligible. In some cases, too much attenuation may be provided by an HPD for a particular noise environment such that the user's hearing is unnecessarily compromised. The safety professional often faces a dilemma in selecting HPDs for the workforce. They are required to provide adequate attenuation for the excessive noise threat; at the same time they should provide safety for warning sounds allowing the worker to hear important signals and/or speech communications. The safety officer faces a dilemma of under protection versus overprotection.

A review of patent applications for ear protectors reveals patents going back to 1946. There are presently several hundred patents addressing the issue of protecting human ear from excessive noise.

Most of the ear protectors are simply devices which occlude the ear with foam or another pliable material. They do not allow for any variability of the attenuation level. They are referred to as "passive ear attenuators". On the other hand, another category of HPDs are referred to as active. These are devices which are noise level dependent and vary the attenuation level with the incoming noise level.

The impetus for the development of variable HPDs were two reports; one by Casali, J. G. and Gerges, S., "Protection and enhancement of hearing in noise", in Williges, R. C., Ed. Reviews of Human Factors and Ergonomics, Vol. 2. Human Factors and Ergonomics Society Santa Monica, Calif., 7, 195-240, (2006) ("Casali 2006"); and Suter, A. H., and the second one; "The effects of hearing protectors on speech communication and the perception of warning signals" (AMCMS Code 611102.74A0011), Aberdeen Proving Ground, Md.: U.S. Army Human Engineering Laboratory, 1-32. (1989) ("Suter 1989").

The Variphone™ is one such example of an adjustable-valve design and is constructed from a custom-molded impression of the user's ear canal. The attenuation adjustment range of the device is approximately 20 dB to 25 dB below 500 Hz. At higher frequencies, the range of adjustment decreases, while the maximum attenuation attainable increases slightly. However, this device does not allow for a transparency of the incoming speech sounds or other warning sounds when needed. Also, separate filters need to be inserted to change the attenuation level.

The Sonomax SonoCustom™ is an example of a selectable-damper design. This device can be fitted with a variety of attenuation dampers that provide the opportunity for discretely variable attenuation in a single device, and each damper has distinct spectral attenuation values and NRR.

Furthermore, the SonoCustom™ is not a functional/practical system where the user can quickly adjust the attenuation level as desired.

There is also a full custom-molded option of the acrylic Variphone™ brand earplug as well as the silicone V-SIL™, both of which incorporate a duct into which selectable "filters" are inserted for different attenuation values. Again, the practically of such device is questionable and in its least attenuation mode it still impairs user's detection of important sounds.

Another device is the dB Blocker™ from Custom Protect Ear. This product is a vented, custom-molded earplug that offers different cartridge filters that can be inserted into the vent. Each cartridge comprises a unique damper/filter which affords a specific attenuation spectrum, and the selection of cartridge is based upon an analysis of the wearer's noise exposure and other needs. The cartridge is intentionally not user-replaceable, so the dB Blocker™ is returned to the manufacturer should a cartridge need replacement or changing. This device, therefore, is preset and does not allow the user to select his/her own attenuation level Yet another category are filter-based devices where the user can select different inserts with a constant attenuation. One example is an Etymotic Research E-15 or ER-20 with two inserts; one of 15 dB attenuation level and one with 20 dB.

One more device is a Combat Arms Double End Shooter's ear plugs for military which has the double end which let you choose constant attenuation for indoor range shooting by choosing one end of the ear plugs or use the other end of the plugs to get variable noise reduction for tactical ops, hunting applications, outdoor range work and other situations where situational awareness is important. Again, the Combat Arms ear plug does not allow the user to vary level of sound attenuation as desired.

In U.S. Pat. No. 8,550,206 to Keady et al. involves hearing protection devices capable of tunable acoustic attenuation; "The invention relates further to ear plugs comprising a fluid-containing balloon for occlusion of the ear canal, which are capable of being adjusted for example by modifying fluid composition and/or fluid pressure within the balloon to vary attenuation at different frequencies of the audible sound spectrum." One objection to such a device is that it is difficult to confine the fluid reservoir and another disadvantage is that the fluid body itself can act as a fairly good conductor of sound and thereby defeats to some degree the purpose of the attenuation device. Another foreseeable problem is that the inflated pressure may alter in the ear canal cavity over time as the device will move with time due to balloon flexibility. This may result in fluctuating changes in the attenuation level.

Therefore, it is desirable to develop an ear attenuator that solves all issues of adequate protection and overprotection by allowing the user to have variable control of the attenuation level and to adjust mixtures between environmental sound and amplified sound via a hearing aid or tinnitus device.

It is also desirable to develop an ear attenuator that overcomes the disadvantages of the prior art.

SUMMARY OF THE INVENTION

Accordingly, it is an object of the invention to provide an attenuator that allows for in situ and instantaneous changes of the level of attenuation for those who are in need of ear protection. It is another object of the invention to provide a device that allows the level of attenuation to be changed, so as not to impede communication. It is another object of the invention to provide a device where the user can adjust the amount of attenuation in a variable, continuous fashion from zero attenuation to maximum attenuation. Such change may be made by the user without removing the device from the ear.

As used herein, the term "hearing device" refers to a hearing aid or tinnitus device or other devices which provide sonic enhancement and/or therapy into the ear using sound generation, reproduction and/or amplification provided by sound amplifying electronics. Such hearing devices may be are used to treat sound sensitivity disorders, sleep disorders or other disorders.

Other objects of the invention allow a user to quickly adjust the amount of sound protection and according to the amount of noise in the environment and also according to the need of being able to maintain communication. Other objects of the invention allow for a variable control attenuation device that is easy to use and that allows a user to control the level of attenuation of the device.

Yet further objects of the invention are to provide for easy adjustment of a mixture of sound between environmental sound and sound from a hearing device such as a hearing aid or tinnitus device.

Still further objects of the invention are to enhance directional capabilities of hearing aids by reducing or blocking environmental sounds to allow the user to better focus on sounds amplified by the hearing aid.

These objects of the invention are achieved by providing a variable sound attenuator (VSA) also referred to as a variable control sound attenuator. The VSA comprises a housing, the housing have a passageway through the housing, the passageway allowing for sound to pass through the housing; and a variable control, the variable control able to control the aperture (or width) of the passageway through the housing. In certain embodiments, the housing is hollow. In certain embodiments, the housing is partially hollow and has a channel that allows for sound to pass through it. In certain embodiments, the passageway through the housing is tapered.

In certain embodiments, the housing includes a top housing and a bottom housing. In certain embodiments, the top housing includes an upper vented opening. In certain embodiments, the top housing and bottom housing are interlocked with one another.

In certain embodiments, the bottom housing includes a bottom vent opening. In certain embodiments, the housing is made of a plastic material. In certain embodiments, the housing is made of hard plastic or a plastic alloy that is durable. In certain embodiments, the housing has a cylindrical or a conical shape. In certain embodiments, the housing has a tubular shape.

In certain embodiments, the variable control is a cap that rotates around the top housing. In certain embodiments, the variable control rotates with the top housing. In certain embodiments, the top of the variable control is ribbed and has ribs on it. In certain embodiments, the ribs are able to provide friction for a user, who wishes to turn the variable control.

In certain embodiments, the top of the variable control has a position indicator. In certain embodiments, the top of the variable control has a click to confirm an open or closed position of the attenuator.

In certain embodiments, the VSA further comprises a locking fin that prevents twisting of the variable control. In certain embodiments, the variable control located within the housing includes foam or any other attenuating material. In certain embodiments, the foam or any other attenuating material limits or prevents sound from passing through it.

In certain embodiments, the VSA further comprises a separator plate within the housing. In certain embodiments, the separator plate separates the foam or any other attenuating material in the bottom housing from the foam or any other attenuating material in the top housing.

In certain embodiments, the foam or any other attenuating material is located in both the top housing and the bottom housing. In certain embodiments, the foam or any other attenuating material in the top housing and bottom housing has the same density. In certain embodiments, the foam or any other attenuating material in the top housing and bottom housing has different density.

In certain embodiments, the attenuating foam or any other attenuating material has an opening and wherein, when the variable control is in the open position, the opening in the attenuating foam or any other attenuating material is aligned with the passageway in the housing, and when the variable control is in the closed position, the opening in the attenuating foam or any other attenuating material is not aligned with the passageway in the housing, such that the attenuating material blocks the passageway and prevents or reduces the passage of sound.

In certain embodiments, the opening the attenuating foam or any other attenuating material is the same size as the opening in the top housing and in the bottom housing.

In certain embodiments, the attenuating foam or any other attenuating material rotates via the variable control. In certain embodiments, the attenuating foam or any other attenuating material can partially block the passageway, so that the variable control is in the half open position. In certain embodiments, a user can control the amount of attenuation, and thus, can control the amount of blocking of the passageway by the attenuating foam.

In certain embodiments, the top housing includes a notch to lock the separator plate. In certain embodiments, the notch limits the variable control to having at most a 180 degrees rotation. In certain embodiments, the notch limits the top housing to having at most a 180 degrees rotation upon the bottom housing. In certain embodiments, the notch of the top housing can have any degree between 0 degree and 360 degrees.

In certain embodiments, the attenuator further comprises a wax guard configured into the attenuating foam or any other attenuating material. In certain embodiments, the wax guard prevents wax formed in a user's ear from entering the attenuator device.

In certain embodiments, the attenuator further comprises an earpiece, the housing being connected to the earpiece. In certain embodiments, the housing is connected to the earpiece via a nub, a portion of the nub being retained by the earpiece. In certain embodiments, the nub contains a passageway allowing for the passage of sound.

In certain embodiments, the earpiece is made of soft silicone custom earmold. In certain embodiments the attenuator is made from any other moldable material. In certain embodiments, the earpiece is, in one embodiment, a domed silicone multiple tulip tip earpiece.

In certain embodiments, the housing has an offset nozzle that allows for better anatomical fit into an ear. In certain embodiments, the housing is made of only two pieces. In certain embodiments, the two pieces include a top housing having attenuating material and a bottom housing having additional attenuating material.

In certain embodiments, the housing is a one-piece housing that is fused together and can turn.

In certain embodiments, a user can adjust the variable control in a variable, continuous fashion or in a discrete controlled fashion from zero attenuation to maximum attenuation without removing the device from the ear.

Other objects of the invention are achieved by providing a VSA comprising: a housing, the housing have a passageway through the housing, the passageway allowing for sound to pass through the housing; and a variable control, the variable control able to control the size of the aperture of the passageway through the housing, such that the passageway is in a first position where the passageway is fully blocked by an attenuating material controlled by the variable control and is in a second position where the passageway is fully open.

In certain embodiments, the variable control is able to partially block the aperture of the passageway so as to control the amount of attenuation in the attenuator.

Other objects of the invention are achieved by providing a VSA comprising: a housing, the housing have a passageway through the housing, the passageway allowing for sound to pass through the housing; a variable control, the variable control able to control the size of the aperture of the passageway through the housing; and a motor, the motor able to actuate the variable control so as to control the size of the aperture of the passageway through the housing. Such electronically driven variation of the size of the opening of the aperture represents an active variable sound attenuator in contrast with a manually controlled aperture described above.

In certain embodiments of an active VSA, such electronically controlled size of the aperture is controlled automatically by adjusting the size of the aperture based on the sound level in the environment.

In another embodiments of an active VSA, such electronically controlled size of the aperture is controlled by the user of an active VSA with a remote controlled device In certain embodiments, the VSA further comprises an input device, the input device being able to control the motor.

In certain embodiments, the housing has a ribbed upper portion.

In certain embodiments, the VSA further comprises a gear, wherein the gear interacts with the ribbed upper portion of the housing to turn the housing radially to control the size of the aperture of the passageway through the housing.

In certain embodiments, the VSA further comprises a pin that is able to actuate the housing to control the size of the aperture of the passageway through the housing.

In certain embodiments, the VSA further comprises a battery, a chip/electronics, and a receiver, such as an antenna. In certain embodiments, the receiver works on radio signals. In other embodiments, the receiver works on BLUETOOTH signals. In certain embodiments, the receiver works on any wireless signal to activate the mechanism responsible for changing the size of the aperture.

In certain embodiments, the input device is an elastic bracelet. In certain embodiments, the input device includes an on/off button and a switch, so as to control the variable control sound attenuator. In certain embodiments, the switch is a rocker switch.

In certain embodiments, the input to the receiver is the level of the incoming environmental sound. The decibel of the detected sound activates the variable attenuator and automatically changes the size of the aperture, thus changing the level of the attenuation.

Still other objects of the invention are achieved by providing a variable control sound attenuator for a hearing device having a housing with a first housing and a second housing, the first housing being rotatable relative to and engaged with the second housing. The first housing further being hollow and cylindrical and containing a first housing passageway therein, the first housing passageway extending through the first housing. The second housing is hollow and cylindrical and contains a second housing passageway therein, the second housing passageway extends through the second housing. Rotation of the first housing provides a variable alignment between the first housing passageway and the second housing passageway thereby providing a variable control of sound transmission through the sound attenuator. The rotation to align the first housing passageway and the second housing passageway provides an open passageway permitting sound transmission therethrough. Rotation to not align the first housing passageway and the second housing passageway provides a closed passageway blocking sound transmission therethrough. The device further includes a hearing aid or a tinnitus device.

In some embodiments the variable control sound attenuator adjusts a balance between environmental sound and sound from the hearing device to control the degree of environmental sound in a mixture of sounds.

In other embodiments an earpiece has an opening therethrough, the earpiece extends from the second housing and is being radially offset from the center of the second housing. The opening connects with the second housing passageway. The hearing device is connected to the variable control sound attenuator and is configured to transmit sound through the opening of the earpiece.

In other embodiments a soft tip surrounds the earpiece.

In yet other embodiments the first housing passageway is semi-cylindrical.

Further embodiments include an element provided on the first housing which is stopped by stops on the second housing to limit rotation of the first housing on the second housing.

In still other embodiments a motor is engaged with the first housing to rotate the first housing and control the alignment between the first housing passageway and the second housing passageway.

In yet other embodiments the housing has a ribbed upper portion and the motor is provided with a gear which is engaged with the ribbed upper portion to turn the housing radially to control the alignment between the first housing passageway and the second housing passageway.

In further embodiments the input device actuates the motor.

In still further embodiments a sound attenuating material is in the first housing, with the first housing passageway extending therethrough.

In yet another embodiment a sound attenuating material is in the second housing, with the second housing passageway extending therethrough.

In still further embodiments the first housing passageway is radially offset from the center of the first housing and the second housing passageway is radially offset from the center of the second housing.

In yet another embodiment the hearing device is a hearing aid and the hearing aid includes a microphone which captures sound with greater emphasis from a direction transverse to the second passageway.

Other objects are achieved by providing a variable control sound attenuator and hearing device configured to be worn by a user. The device includes a housing and a first passageway in the housing. A second passageway in the housing is configured to connect to the hearing device to receive amplified sound. An adjustor is connected to the housing and operable to move between open and closed positions to change an amount of environmental sound passing through the first passageway.

In one embodiment an earpiece has an opening and is connected to the first and second passageways at the opening such that sound passes through the opening.

In another embodiment the adjustor modifies a size of an aperture through the first passageway between open and closed positions of the adjustor such that the adjustor adjusts a mixture between: the environmental sound passing through the first passageway; and the amplified sound from the hearing device.

In still another embodiment the variable control sound attenuator connects to a hearing aid and the hearing aid comprises a microphone. The microphone may be unidirectional. The microphone may further pick up sound with greater emphasis from a direction being transverse to the first passageway. The direction may be forward facing when the hearing aid and variable control sound attenuator is worn by the user.

In one embodiment the sound amplification device includes a speaker positioned in said second passageway.

Other objects are achieved by providing a hearing aid or tinnitus device having a variable control sound attenuator and configured to be at least partially placed in an ear of a wearer. The device includes a housing and a passageway in the housing. A sound amplification device is configured to transmit amplified sound into an earpiece. An adjustor is operable to move between open and closed positions to thereby adjust a size of an aperture of the first passageway to change a mixture of sound passing into the earpiece, the mixture of sound between environmental sound through the passageway and the amplified sound.

In one embodiment the hearing aid or tinnitus device is a hearing aid and includes a microphone. The sound amplification device amplifies sound received from the microphone;

In one embodiment, the microphone is directional and amplifies sound from a direction transverse to the first passageway.

In another embodiment the earpiece is part of the housing.

In another embodiment, the sound amplification device includes a speaker positioned in the housing.

In yet another embodiment the sound amplification device transmits sound into the earpiece via a second passageway in the housing.

Other objects of the invention and its particular features and advantages will become more apparent from consideration of the following drawings and accompanying detailed description. It should be understood that the detailed description and specific examples, while indicating the preferred embodiment of the invention, are intended for purposes of illustration only and are not intended to limit the scope of the invention.

BRIEF DESCRIPTION OF THE DRAWINGS

FIG. 1 is a perspective view of a variable sound attenuator device located within an ear of an individual;

FIG. 2 is a perspective view of the VSA of FIG. 1;

FIG. 22 is a perspective view of the VSA in FIG. 20.

FIG. 23 is an end view of the VSA of FIG. 20 looking from the end of the VSA that is inserted into the ear.

FIG. 24 is an exploded view of FIG. 22.

FIG. 25 is another exploded view of the device of FIG. 22.

FIG. 29 is an end view of the VSA of FIG. 20 looking from the end of the VSA which is external of the ear.

DETAILED DESCRIPTION OF THE INVENTION

Figure 3A:
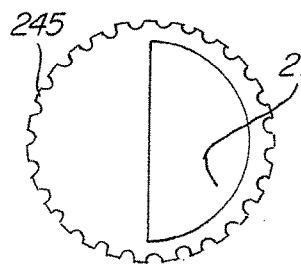
FIGS. 3A-3C is a top view of the VSA of FIG. 2 in various positions.

U.S. Provisional No. 61/790,243, entitled "Variable Noise Attenuator" and filed on Mar. 15, 2013 is herein incorporated into this application in its entirety.

Referring to FIG. 1, a VSA also referred to as an attenuator 200, is shown within the ear of a user 100. The attenuator 200 is shown in additional detail in FIG. 2.

Referring to FIG. 2, the exterior design of an attenuator 200 of an embodiment of the invention is shown. Here, the attenuator 200 is shown having an upper vented opening 215, a top housing 210 with ribs 245, a bottom housing 220, a locking fin 230 that prevents twisting, a narrow extension 240 and a nub 250 for retention in an earpiece. The nub 250 has a bottom vented opening 260 passing through the nub 250. The top housing 210 is able to rotate radially with regards to bottom housing 220, via rotation of the top housing 210 on the bottom housing 220 in the direction of the arrow. The top housing 210 and the bottom housing 220 are shown having substantially the same diameter. In certain embodiments, the diameter of the top housing and bottom housing can vary with respect to one another, such that the device is tapered.

The top housing 210 of the attenuator 200 can be rotated from right to left and from left to right around the circumference of the housing. Such a rotation allow for variable control of the amount of sound that is able to pass through the attenuator. In certain embodiments, the top housing 210 of the attenuator 200 can be rotated 180 degrees. In other embodiments, the top housing 210 of the attenuator 200 can be rotated more or less than 180 degrees.

Referring to FIG. 3A, the top housing 210 is shown in an open position, where the upper vented opening 215 is shown as being fully open. In the open position, a passageway (upper vented opening 215) is shown, allowing for the passage of sound through the housing.

Figure 3B:
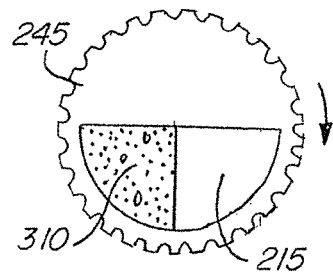

Referring to FIG. 3B, the top housing 210 is shown in a half open position. In a half open position, foam attenuating material 310 is shown as blocking part of the passageway, while allowing for the upper vented opening 215 to be partially open. A user can control the amount of rotation of the variable control so as to select how much of the passageway is open to the passage of sound using the device. In this way, the user controls the level of attenuation of the device.

Figure 3C:
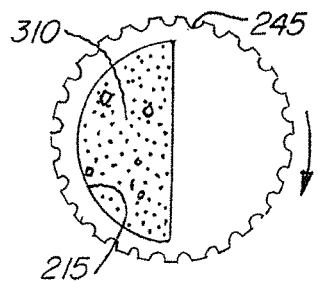

Referring to FIG. 3C, the top housing 210 is shown in a closed position where the foam attenuating material 310 blocks the passageway in the top housing 210. Here, the foam attenuating material 310 blocks the passageway, and thus, blocks or minimizes the sounds from passing through the passageway of the attenuator 200.

Figure 4:
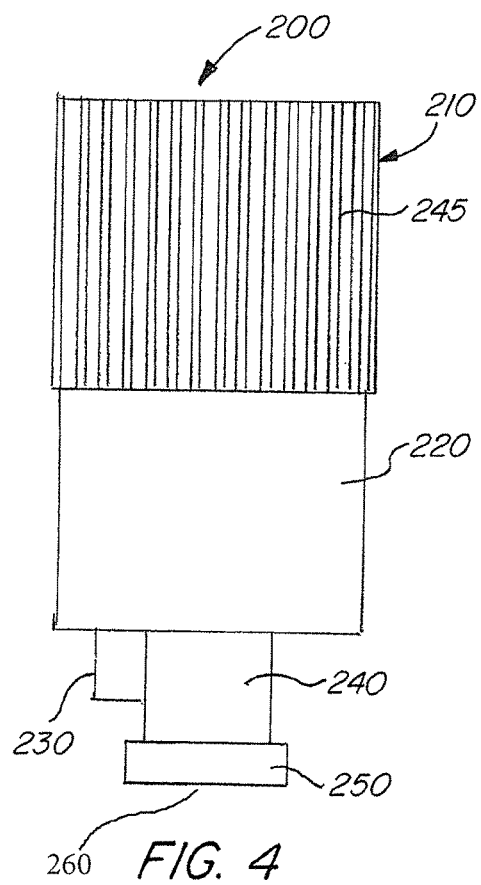
FIG. 4 is a front view of the VSA of FIG. 2.

Referring to FIG. 4, a side view of the attenuator 200 is shown. Attenuator 200 has a top housing 210, which is shown as having ribs 245, a bottom housing 220, a locking fin 230 that prevents twisting, a narrow extension 240 and a nub 250 for retention in an earpiece. The narrow extension 240 and nub 250 allow for the device to fit within a tip and within an ear of a user. The narrow extension 240 and nub 250 have a smaller diameter than top housing 210 and bottom housing 220. Bottom vented opening 260 is also shown passing through the nub 250.

Figure 5:
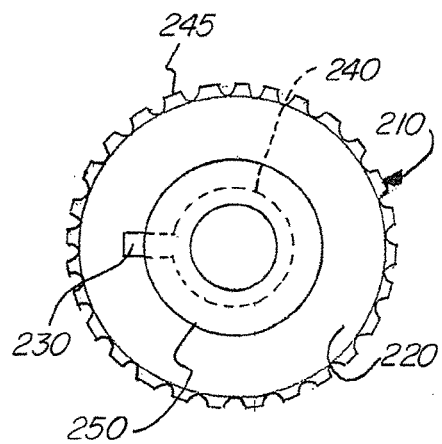
FIG. 5 is a top view of the VSA of FIG. 2.

FIG. 5 shows a top view of the attenuator 200 of FIG. 2. In FIG. 5, top housing 210, ribs 245, locking fin 230 and bottom housing 220 are shown. The locking fin 230 is shown such that the locking fin prevents twisting of the attenuator 200.

Figure 6:
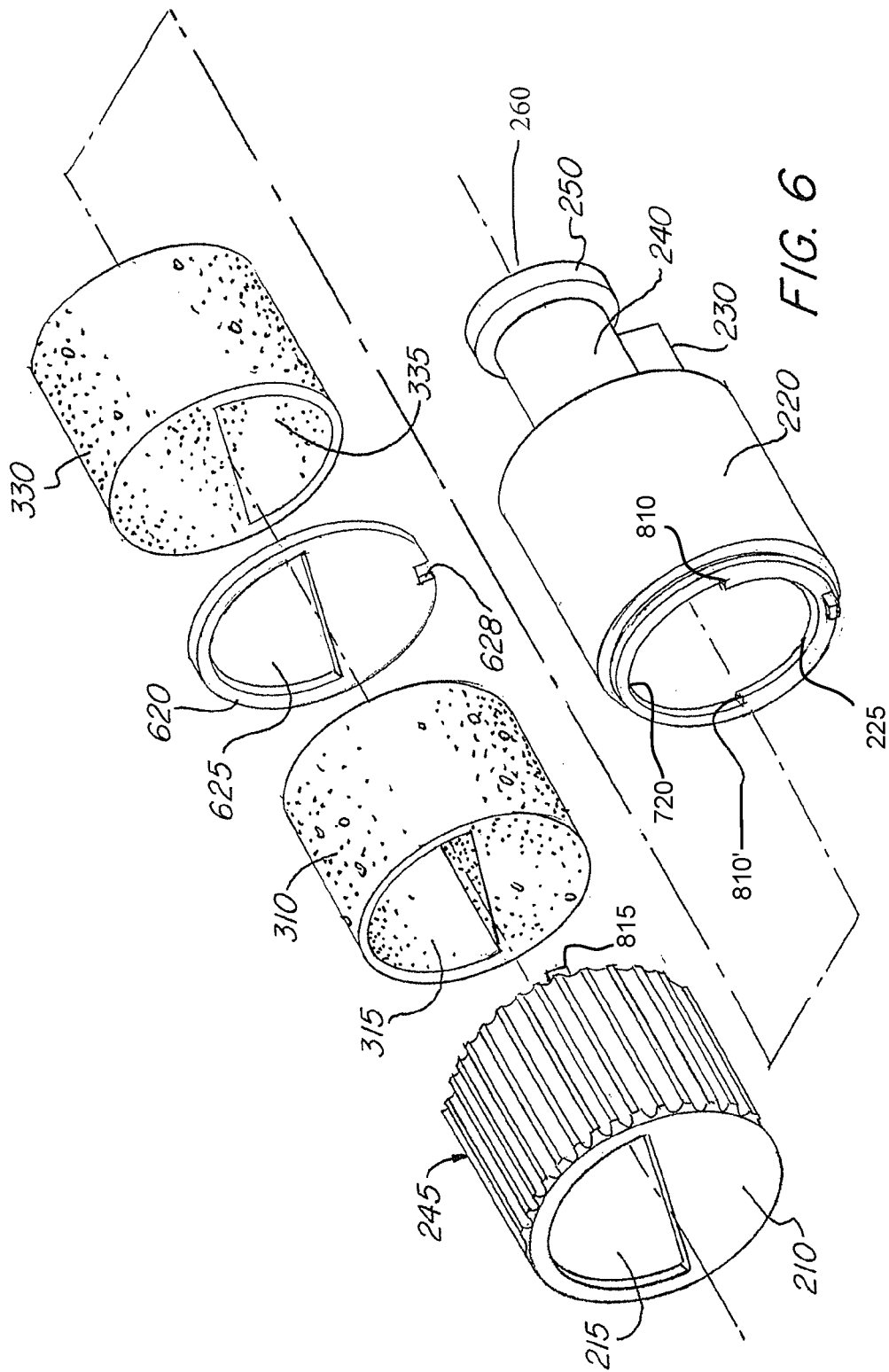
FIG. 6 is an exploded perspective view of the VSA of FIG. 2.

FIG. 6 schematically illustrates an exploded view of the attenuator of FIG. 2. In FIG. 6, top housing 210 is shown having ribs 245. Foam attenuating material 310 is shown having vented opening 315. Separator plate 620 is shown with vented opening 625. Separator plate 620 has a notch 628, which interacts with tab 228 in bottom housing 220. Also shown is foam attenuating material 330 having a vented opening 335. Foam attenuating material 310 is housed in top housing 210 and foam attenuating material 330 is housed in bottom housing 220. The separator plate 620 separates the foam attenuating material 310 and 330.

Figure 7:
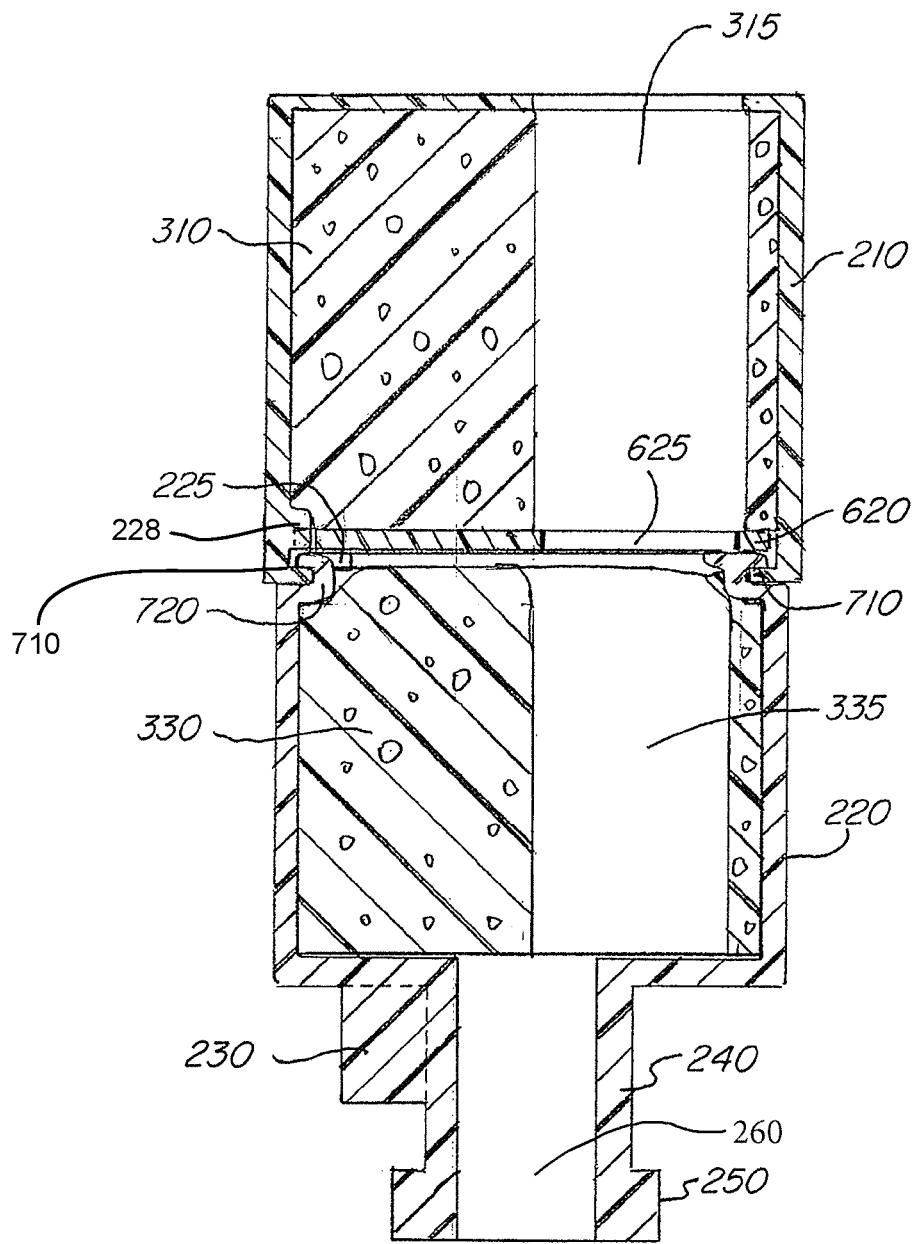
FIG. 7 is a cross section view of the VSA of FIG. 2.

FIG. 6 also shows the bottom housing 220 having an engagement portion 225, the engagement portion having a rim 720 and engaging with the bottom member 710 of the top housing 210 (as seen in FIG. 7) and allowing the top housing 210 to rotate on top of the bottom housing 220. Top housing 210 also has a tab 228, which is able to engage with notch 628 in the separator plate 620. This locks the top housing 210 and separator plate 620 to one another.

FIG. 6 also is shown having locking fin 230, extension 240 and bottom vent opening 250. The top housing 210 and bottom housing 220 have a passageway, which is shown as being hollow and extends from the upper vented opening 215 through the opening in the foam material in the upper and lower housing and through the bottom vented opening 260.

FIG. 7 schematically illustrates a cross section view of the attenuator 200. Here, the top housing 210 is shown as being held in place by engagement portion 225, which is located on the top of bottom housing 220. Separator plate 620 is shown in between the top housing 210 and bottom housing 220 and supporting foam attenuating material 310. Foam attenuating material 330 is shown in bottom housing 220.

Locking mechanisms can be used to lock the top housing 210 and bottom housing 220 to one another. The locking features are important as once a user sets the level of attenuation, the locking features allow the user to lock the device in place so as to keep the required level of attenuation, so that is kept constant as a user moves about. For example, this allows a hunter or soldier who is on the move, to set the required level of attenuation.

Also in FIG. 7, the vented openings 315, 625, 325 and 260 are also shown so as to form a passageway through the attenuator 200. This allows for sound to pass through the attenuator 200.

Figure 8:
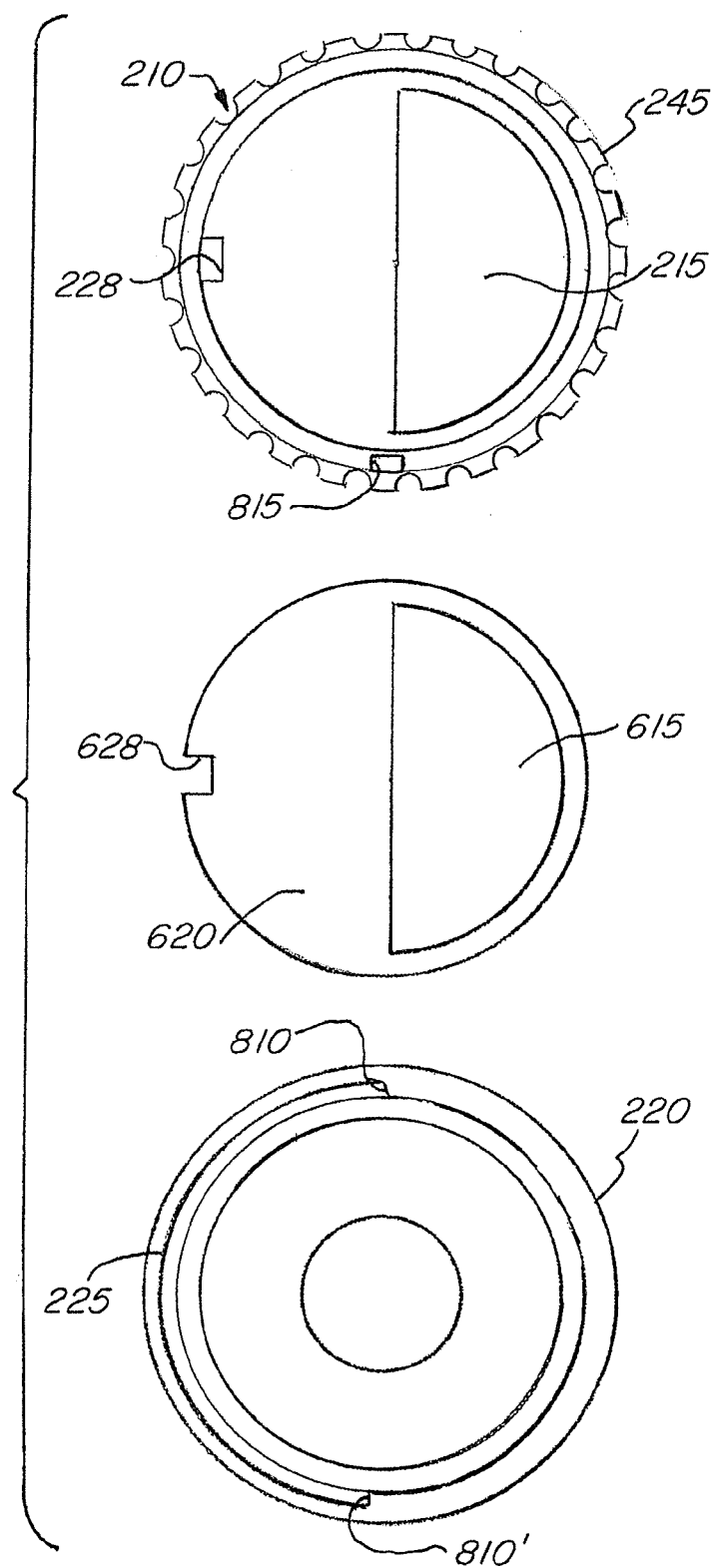
FIG. 8 is an internal exploded view of the VSA of FIG. 2.

FIG. 8 schematically illustrates an internal top exploded view of the attenuator 200. The top housing 210 is shown having ribs 245 and a passageway 215. The separator plate 620 is also shown having notch 628 and vented opening 625. The bottom housing 220 is shown below having an engagement portion 225 for engaging the top housing 210.

An element 815 is provided with the top housing 210 and separator plate 620 to limit 180 degree rotation. The element 815 is stopped by stops 810 and 810' on the bottom housing 220 to limit rotation to 180 degrees.

Figures 9, 10:
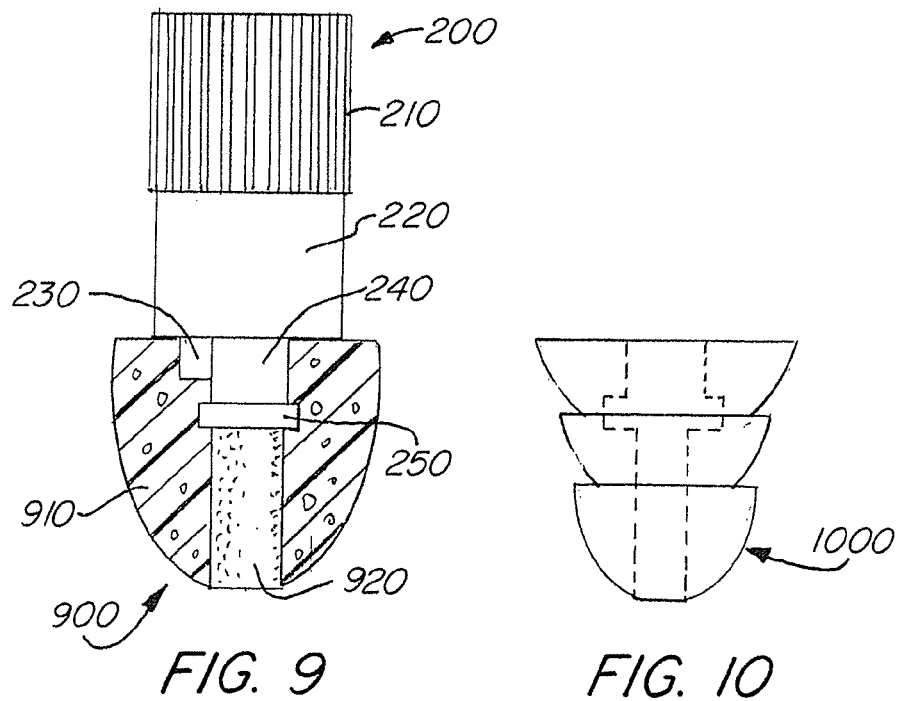
FIG. 9 is a side view of a VSA of FIG. 2 inserted into a tip for insertion into an ear, with the tip shown in cross-section.
FIG. 10 is a side view of a multiple tulip tip for insertion into an ear.

FIG. 9 schematically illustrates a side view of attenuator 200 being inserted into a tip 900 for insertion into an ear. In certain embodiments, tip 900 is made of foam. In certain embodiments, tip 900 has a passageway 920 and is made of attenuating material 910. FIG. 9 also shows how the attenuator snugly fits within the tip 900.

FIG. 10 schematically illustrates a domed silicone multiple tulip 1000 tip. Such a tip can be used in place of tip 900 in certain embodiments of the invention. The domed silicone multiple tulip 1000 tip can be tapered in certain embodiment and can have various configurations so as to fit within the ear of a user.

Figure 11:
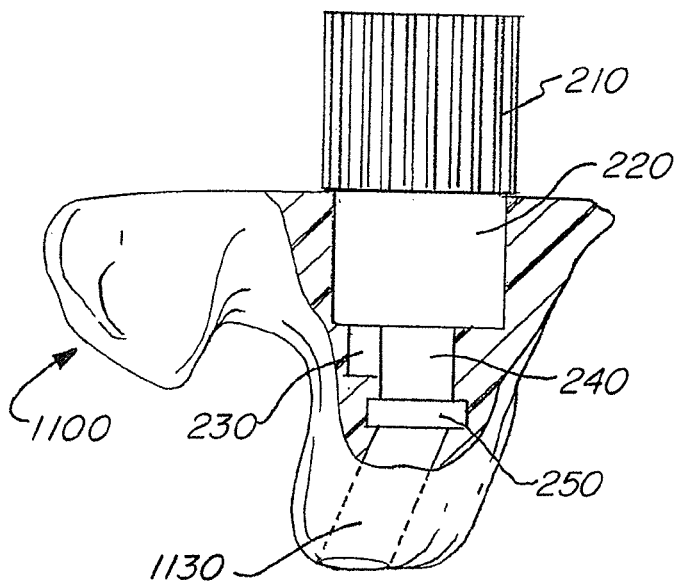
FIG. 11 is a side view of a VSA of FIG. 2 inserted into a tip for insertion into an ear showing the tip in partial cross-section.

FIG. 11 schematically illustrates a side view of attenuator 200 being placed within a soft silicone custom earmold 1100. The soft silicone custom earmold 1100 can be used in place of tip 900 in certain embodiments of the invention. The earmold 1100 has a passageway 1130 that is angled. In certain embodiments, the earmold 1100 has a passageway 1130 that fits within the direction of a user's ear canal. Other embodiments of the invention include a foam mushroom tip of various sizes. All of these earmolds are used to interact with a user's ear and have varying shapes and sizes to comfortably engage with a person's ear.

In certain embodiments, the attenuator 200 is a custom or a non-custom device. In a custom shell fitted application, a custom fitted mold obtained from an impression taken of the ear is positioned into the concha and/or the ear canal. The shell consists of a free passage from the end of the canal part to the surface of the shell facing the entrance of the concha. Such entrance is covered with the Attenuator Core (AC).

In certain embodiments, a dialing knob is provided to allow for a continuous adjustment of the amount of attenuation; i.e., by turning the knob in one direction the aperture of the AC closes the free passage for maximum attenuation while turning the knob in opposite direction opens the AC and the attenuation decreases to minimum. The gradual closing, introduces various attenuation factors depending on the position of the AC at the free passage aperture.

Such change of attenuation is described as "dialing" a desired attenuation. However, any other way of changing attenuation can be also considered. For example a sliding switch can be another way of changing attenuation. In another embodiment a manual or automatic variable switching modality can be conceived as an alternating possibility. Yet, in another embodiment a step like attenuation change can be also considered, such that a user can vary the level of attenuation in discreet steps.

Figure 12:
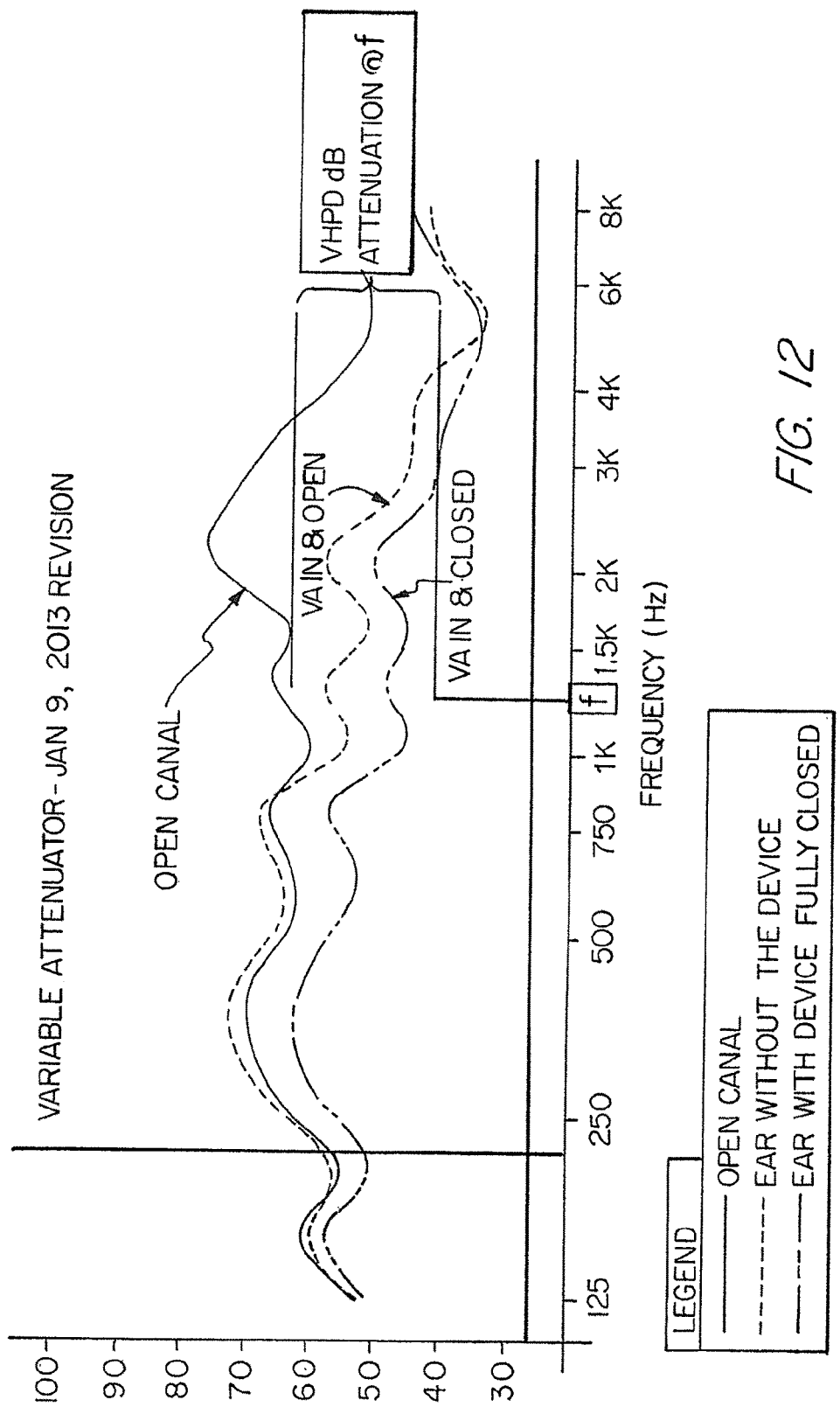
FIG. 12 is a graph comparing attenuation in an ear with and without the device.

FIG. 12 illustrates a graph comparing attenuation in an ear with and without the device. FIG. 12 is shown having a Y-axis in decibels (dB) and an X-axis measured in Hertz (Hz). Shown in FIG. 12 is a line where the ear canal is open. Shown is another line is where the attenuator is in the ear and in the open position, and shown in another line is where the attenuator is in the ear and in the closed position. The difference between the two lines represent total amount of attenuation (from approximately 10 dB at 500 Hz to about 30 dB at 3000 Hz). The Difference between the line where the ear with and without the device represents occlusion effect.

FIG. 12 also shows that up to 100 Hz, there is no insertion loss. After 100 Hz, the insertion loss impedes transmission/attenuates sounds.

In the fully open position the attenuator core has a very low attenuation (close to zero) allowing for maximum external sound to be transmitted to the ear. The extreme opposite position provides for maximum sound protection from the external sound.

In certain embodiments of the invention, the device can create an attenuation difference of greater than 20 decibels, which is remarkable for a device of this size. Most prior art devices lacking variable control have only been able to produce an attenuation difference of approximately 3-6 decibels (dB).

FIGS. 13-16 schematically illustrate a perspective view of an attenuator of another embodiment of the invention.

Figure 13:
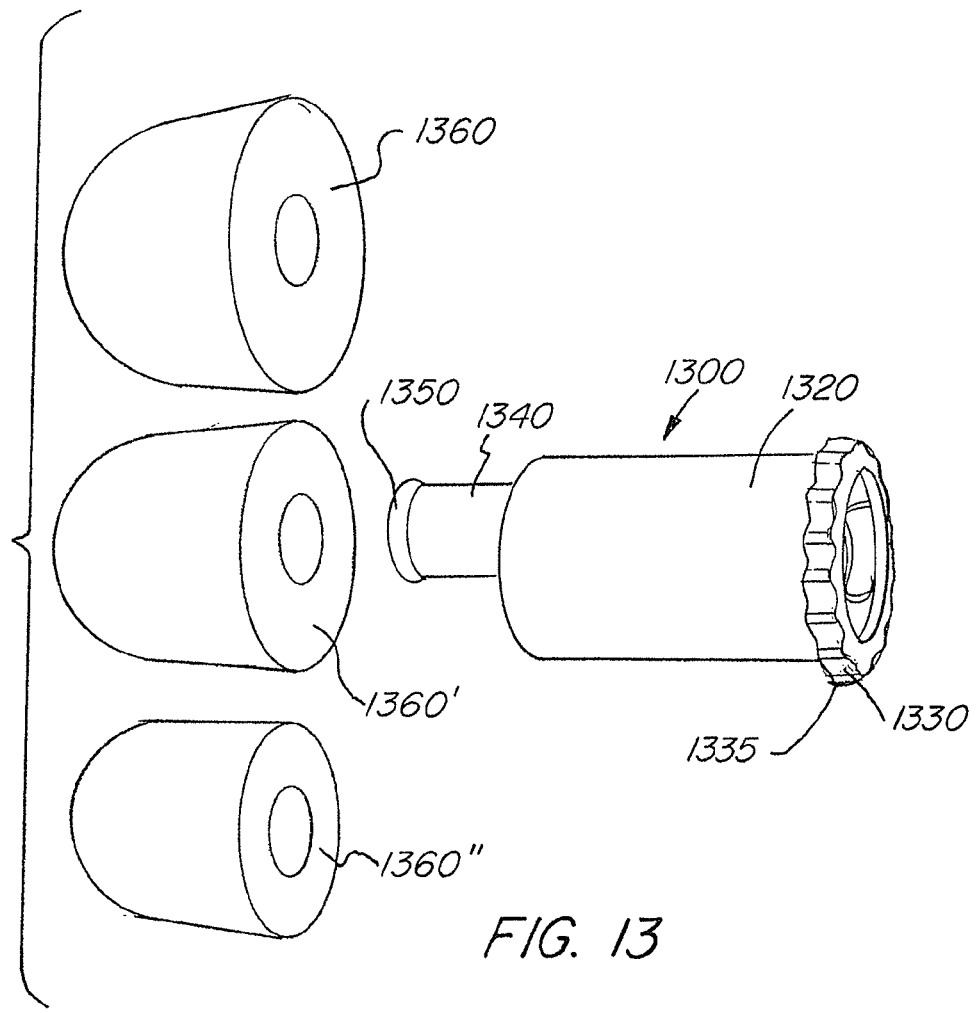
FIG. 13 is a perspective view of a VSA of an embodiment of the invention.
Figure 14:
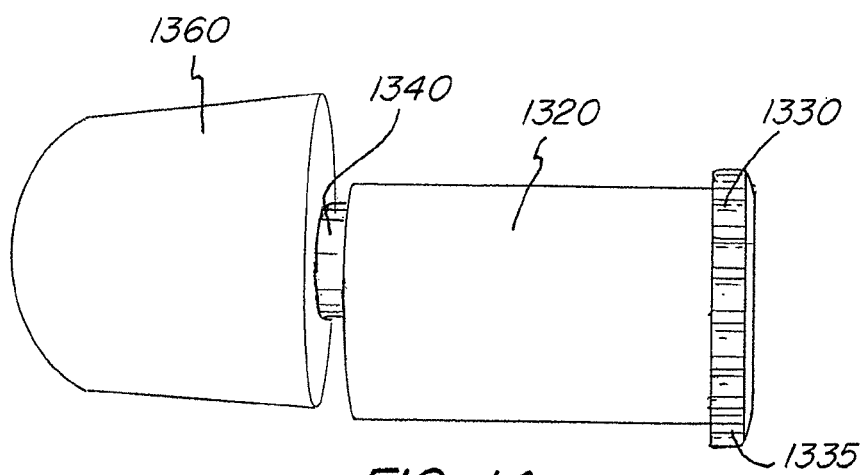
FIG. 14 is a perspective view of the VSA of FIG. 13.

Referring to FIG. 13, attenuator 1300 is shown having an upper body 1320 and a lower body 1340 and a vent opening 1350. A variable control 1330 is attached to the upper body 1320 and is shown as having ribs 1335. The vent opening 1350 is shown as being able to mate with in a male-female configuration with tips 1360, 1360' and 1360", each being of a different size and shape. FIG. 14 schematically shows the attenuator 1300 inserted into tip 1360. The size and shape of tips 1360, 1360' and 1360" can be customized to a particular user's ear.

Figure 15:
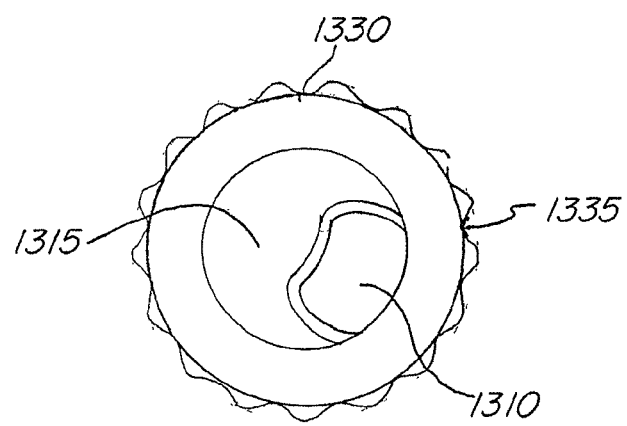
FIG. 15 is an end view of the VSA of FIG. 13 in a closed position.
Figure 16:
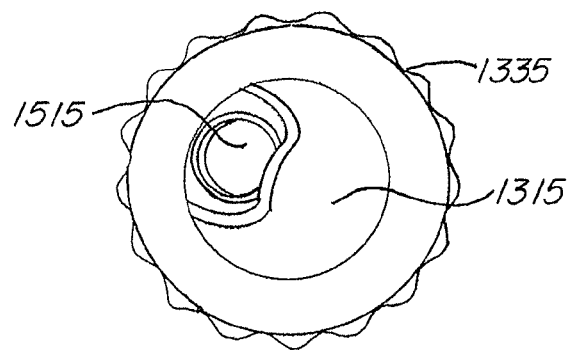
FIG. 16 is an end view of the VSA of FIG. 13 in an open position.

FIG. 15 shows a top internal view of attenuator 1300 in a closed position whereby attenuator 1300 has a passageway 1310 that is shown as being blocked by foam attenuating material 1315. FIG. 16 shows the passageway being in an open position, whereby opening 1515 is provided so as to show that the passageway 1310 is open for sound to pass through it.

The attenuator shown in FIG. 15 is a two-piece attenuator that has a unique snapping mechanism, such that the mechanism allows the two pieces to be snapped together, such that in one way, the snapping of the two pieces allows for right rotation on the variable control, and in another way, the snapping of the two pieces allows for left rotation on the variable control. The manner in which the two pieces snap together allows for the orientation of twist of the attenuator.

Also as shown in FIGS. 15 and 16, the opening 1515 and passageway 1310 have a unique shape, such that the open is able to be open or closed with either a device that is snapped to allow for right rotation or for left rotation (right hand device or left hand device).

In certain embodiments of the invention, the attenuator device can be engaged with various tips for insertion into the ear.

In a certain embodiments, the attenuation is varied by user "dialing" an attenuator plate/diaphragm with preset attenuation factor. Each turn introduces another layer of such a diaphragm, introducing an additional attenuation. In such fashion, each layer increases the total attenuation factor when dial one way and decreases attenuation level when dial the opposite way.

In certain embodiments of the invention, the attenuator device can be applied to one or more of a person's ears. The attenuator device for the right ear can be highlighted with a red color and the VSA device for the left ear can be highlighted with a blue color or vice versa, so that a person will know which ear to apply the attenuator. Other colors can be used for the various VSA devices.

In certain embodiments, the left ear and right ear attenuator devices are mirror images or are chiral versions of each other, such that the left ear and right ear attenuator devices are a non-superposable mirror image of one another.

In certain embodiments of the invention, attenuation can be controlled by twisting the knob at the top of the attenuator device.

In certain embodiments, the insertion tip into a person's ear is disposable. In other embodiments, the insertion tip can be custom made and/or be reusable.

According to other embodiments, a user can adjust the amount of attenuation in a series of steps, such that there are preset levels of attenuation in the attenuator. In this manner, for example, a user can adjust attenuation levels from 0 to 20% to 40% to 60% to 80%, so as to vary the amount of attenuation in a discrete, controlled way.

In certain embodiments of the invention, a remote control device can change the ratio between the open passage and the attenuator core/insert which will result in a variable attenuation delivered to the protected ear. And finally an automatic switching triggered by speech or a level of external sound can be entertained.

Figure 17:
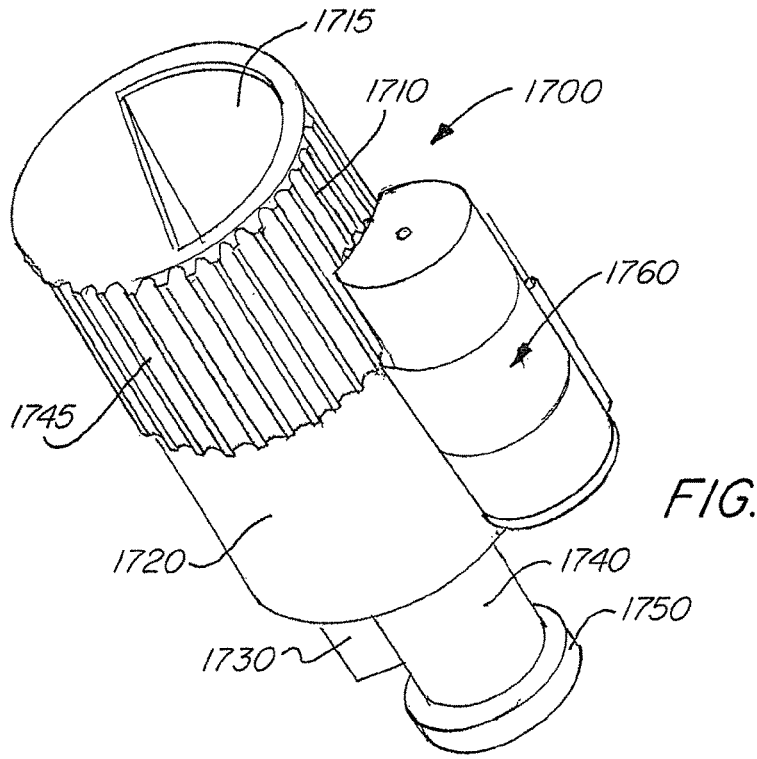
FIG. 17 is a perspective view of the VSA having a motor to control the amount of attenuation within the device.

This is shown in FIG. 17, which illustrates an embodiment of the invention. Referring to FIG. 17, an attenuator 1700 is shown. Here, the attenuator 1700 is shown having an upper vented opening 1715, a top housing 1710 with ribs 1745, a bottom housing 1720, a locking fin 1730 that prevents twisting, a narrow extension 1740 and a nub 1750 for retention in an earpiece. The top housing 1710 is able to rotate radially with regards to bottom housing 1720, via rotation of the top housing 1710 on the bottom housing 1720. The top housing 1710 and the bottom housing 1720 are shown having substantially the same diameter. In certain embodiments, the diameter of the top housing and bottom housing can vary with respect to one another, such that the device is tapered.

The top housing 1710 of the attenuator 1700 can be rotated from right to left and from left to right around the circumference of the housing. Such a rotation allow for variable control of the amount of sound that is able to pass through the attenuator. In certain embodiments, the top housing 1710 of the attenuator 1700 can be rotated 180 degrees.

In certain embodiments, the top housing 1710 of the attenuator 1700 can be rotated up to 360 degrees.

Also shown in FIG. 17 is motor housing 1760, the motor housing 1760 housing various components that actuate the top housing 1710 of the attenuator.

Figure 18:
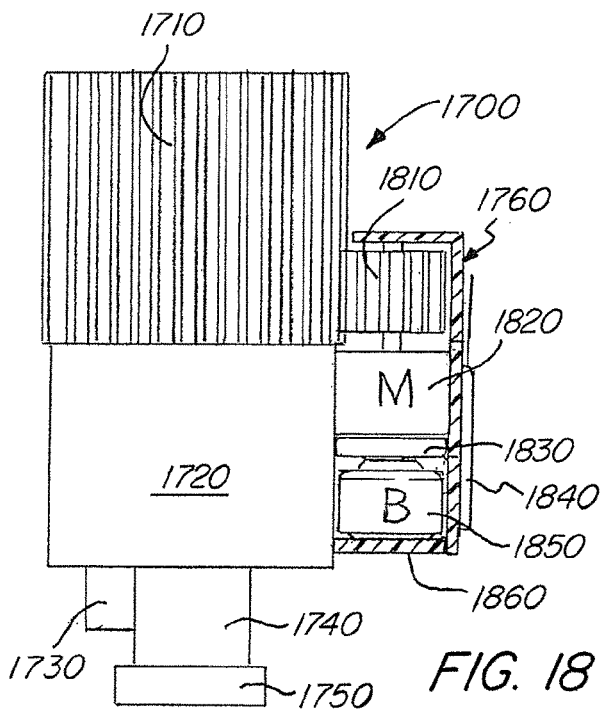
FIG. 18 is a side cutaway view of the VSA of FIG. 17.

Referring to FIG. 18, a front view of the attenuator 1700 is shown. FIG. 18 illustrates that gear 1810 is used to turn the top housing 1710 of the attenuator 1700. As shown, the fibs 1745 interact with the gear 1810 to actuate the top housing 1710.

Also shown in FIG. 18 are motor 1820, chip/electronics 1830, antenna 1840, battery 1850 and support 1860. The motor 1820 actuates the gear 1810 to turn the top housing 1710. The battery 1830 is used to power the motor 1820 and is replaceable. Antenna 1840 is used to receive signals from an input device and the chip/electronics 1830 processes the signals in order to control the motor 1820 to have the motor actuate the gear 1810 to turn the top housing 1710.

Figure 19:
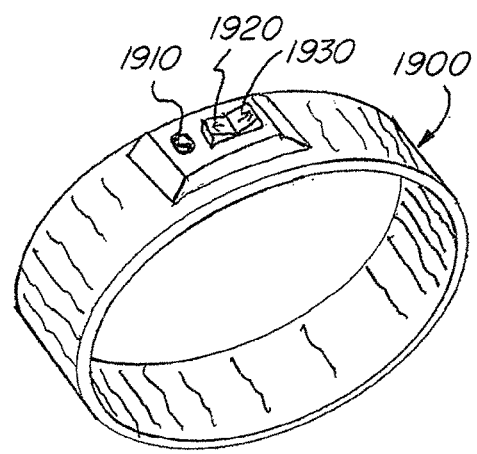
FIG. 19 is a perspective view of an input device to control the VSA of FIG. 17.

In FIG. 19, an example of an input device 1900 that controls the attenuator 1700 is shown. Input device 1900 is shown as having an on/off button 1910 and a switch 1920/1930, the switch 1920/1930 being able to control the direction of the attenuation of the attenuator 1700.

The input device 1900 is shown as an elastic wrist band. Other embodiments of an input device are also contemplated as part of the invention.

Referring to FIGS. 20-25 a variable sound attenuator (VSA) 2002 is connected to a hearing device 2001. The variable sound attenuator allows adjustment and control the amount of ambient sound which is delivered directly to the ear bypassing the amplification provided by the hearing device. The attenuator allows the wearer to vary the amount of direct environmental sound which enters the ear canal without being processed by the amplification provided by the hearing device.

Figure 20:
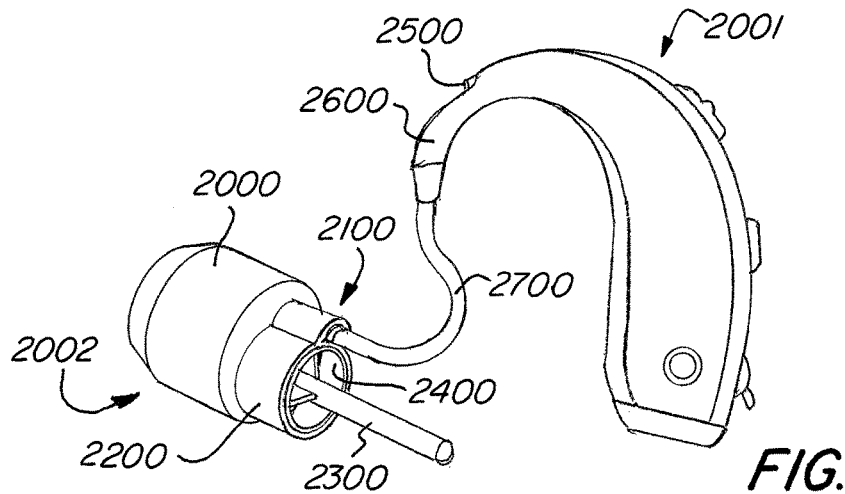
FIG. 20 is a perspective view of a hearing device connected to a combination VSA and in the ear receiver.

In the embodiment depicted in FIG. 20 the hearing device is a hearing aid with a microphone 2500. The hearing aid amplifies and transmits sound from the microphone through a tube 2700 running through passageway 3000 which is part of the variable sound attenuator 2002. The hearing aid depicted is a behind the ear (BTE) hearing aid and the speaker may be located at one end 2600 of tube 2700 within the hearing aid. The behind the ear portion of the hearing aid includes an amplifier connected to the speaker and to the microphone.

The tube 2700 carries the amplified sound into the ear of the wearer. The VSA 2002 may be retrofitted onto existing BTE hearing aids by inserting the tube into passageway 3000. The VSA includes a housing 2100 that includes first 2400 and second 2200 housings, where rotation of the first housing 2400 adjusts a size of an aperture 2800 allowing sound to enter the earpiece 2000. As shown in FIG. 23, the complete alignment of passageways 3100 and 3200 provides a fully-open aperture 2800, allowing for maximum environmental sound passage. Adjustment of the VSA to change the alignment of passageways 3100 and 3200 will alter the size of the aperture 2800 to thereby adjust the amount of environmental sound that can enter the ear of the wearer. If passageways 3100/3200 are not aligned, aperture 2800 is fully closed, providing maximum attenuation. The adjustment may be done by way of knob 2300, but other adjustment mechanisms are contemplated. Although not shown in the specific embodiment of FIGS. 20-25, a motor such as the one in FIG. 18 may be connected to the VSA to turn the knob 2300 or to adjust the aperture 2800. It is understood that features shown and described in FIGS. 1-19 may be included in any of the attenuator components of the attenuator and hearing aid/tinnitus device.

The combination of the housings and the knob shown creates one example of an adjustor which allows the user to selectively change the size of the aperture 2800 based on the alignment condition between passageway 3200 and passageway 3100. When closed, the adjustor blocks environmental sound from passing into the earpiece and thus the user will hear sounds predominantly from the hearing aid/tinnitus device.

Figure 21:
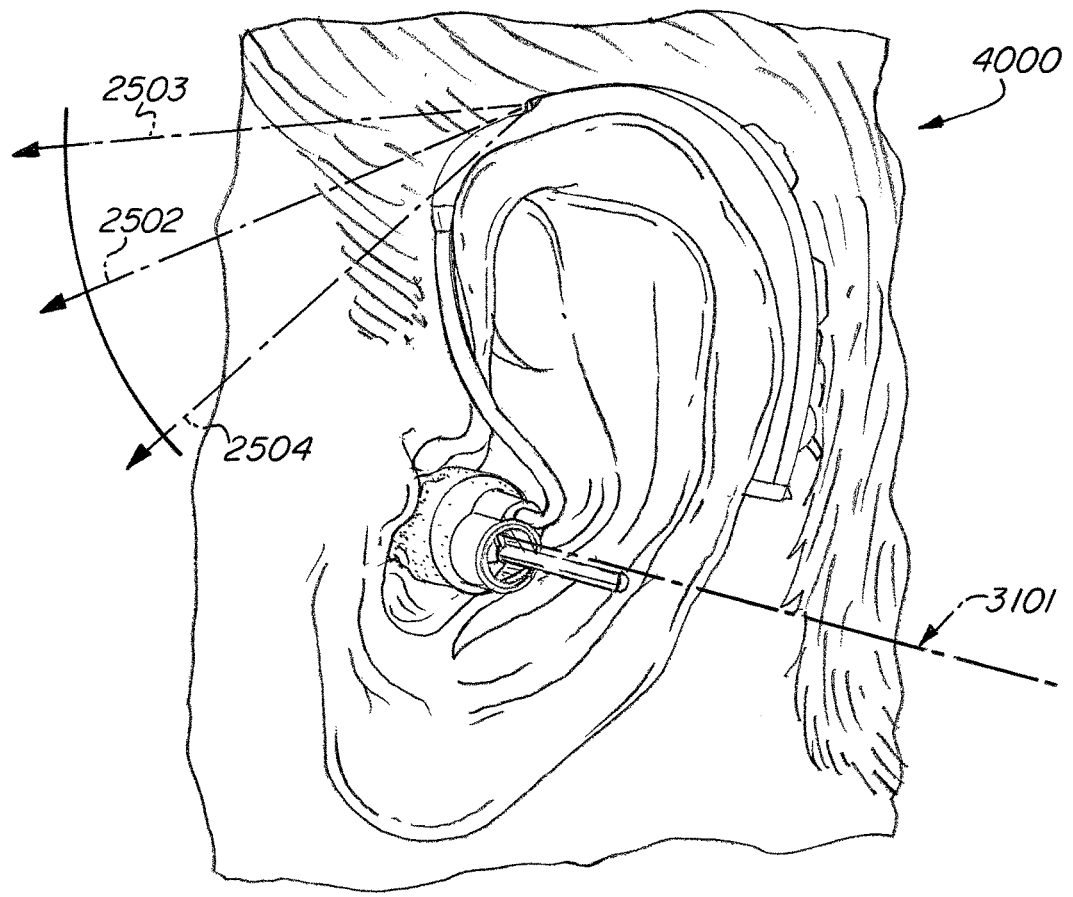
FIG. 21 illustrates the device of FIG. 20 as worn by a user.

Referring specifically to FIG. 21, the adjustment of the aperture 2800 allows for the mixture of environmental and amplified sound to be changed by the user. When combined with a hearing aid having a directional microphone 2500, the user can turn down or turn off environmental sound. For example, the directional microphone may emphasize sounds coming from direction 2502. The directional microphone may emphasize sounds within a range (2503 to 2504) on either side of the primary direction 2502. The direction 2502 (which may be associated with the middle of the range of at 2D or 3D pickup profile) is transverse to axis 3101 which is associated with the VSA. It is understood that the range 2503-2504 may be a two or three dimensional range. One three dimensional pickup range would be a cone shape. Further examples include microphones with other shape pickup patterns such as cardioid and hypercardioid. These patterns generally focus pickup of sound along a central axis (i.e. direction 2502) and a relatively narrow range of angles varying from the central axis. This direction 2502 will generally be aligned with the user's line of sight when applied to hearing aids.

Ambient and environmental sounds may enter the ear of the wearer from many directions, not just along axis 3101, but these sounds would enter the aperture that lines up with axis 3101 if not attenuated or blocked. Therefore, when closing or making aperture 2800 smaller, environmental sounds are de-emphasized or blocked, which changes the mixture of sounds entering the ear of the wearer. When closed, the sound predominantly entering the ear will be from the hearing aid/tinnitus device via passage 3000. This means that the wearer 4000 is more able to use the directional capabilities of the hearing aid by blocking environmental sounds while simultaneously facing the sound source of interest.

The earpiece has an opening that receives the VSA 2002 so that the aperture 2800 and the end of the hearing aid 2900 can pass sound into the ear of the wearer 4000. The earpiece may also be molded to or attached to the VSA as shown in FIG. 11.

The VSA as shown in FIGS. 24-25 includes passage 3000 for the hearing aid and passage 3100 for environmental sounds. Both of these passages in the embodiment shown are positioned in the second housing 2200 of housing 2100. The first housing 2400 includes passage 3200 which is radially offset from center thereof. Channel 2210 receives stop 2220 so the stop 2220 can rotate within the channel 2210. As can be seen, channel 2210 is discontinuous, thus stop 2220 limits the angles of rotation of the first housing 2400 within the second housing 2200.

Figure 26:
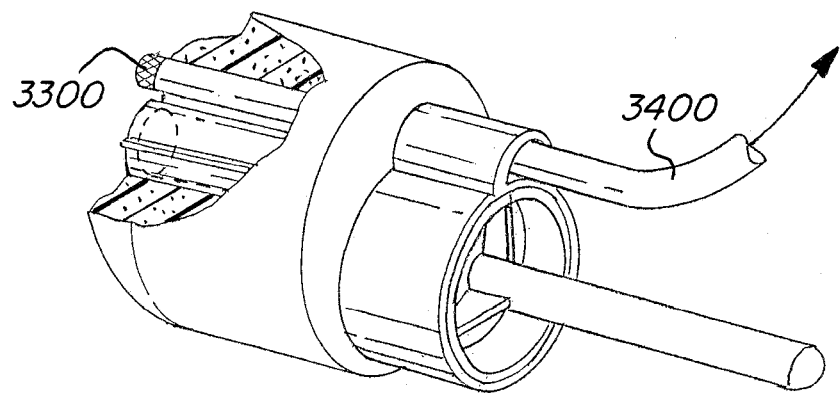
FIG. 26 is a partial cutaway view of a second embodiment of the VSA and a hearing device.

FIG. 26 shows another embodiment where the hearing aid includes a speaker 3300 positioned in the ear. This configuration is often referred to in the industry as receiver in the ear. In this embodiment, tube 2700 is replaced with a wire 3400 which transmits electrical signals to the speaker 3300 instead of the sound that is transmitted through tube 2700. This speaker 3300 allows sound to be transmitted through the VSA via the separate passage 3000 from the environmental sound passage 3100. The adjustor previously described allows the user to adjust a mixture between environmental and amplified sound.

Figure 27:
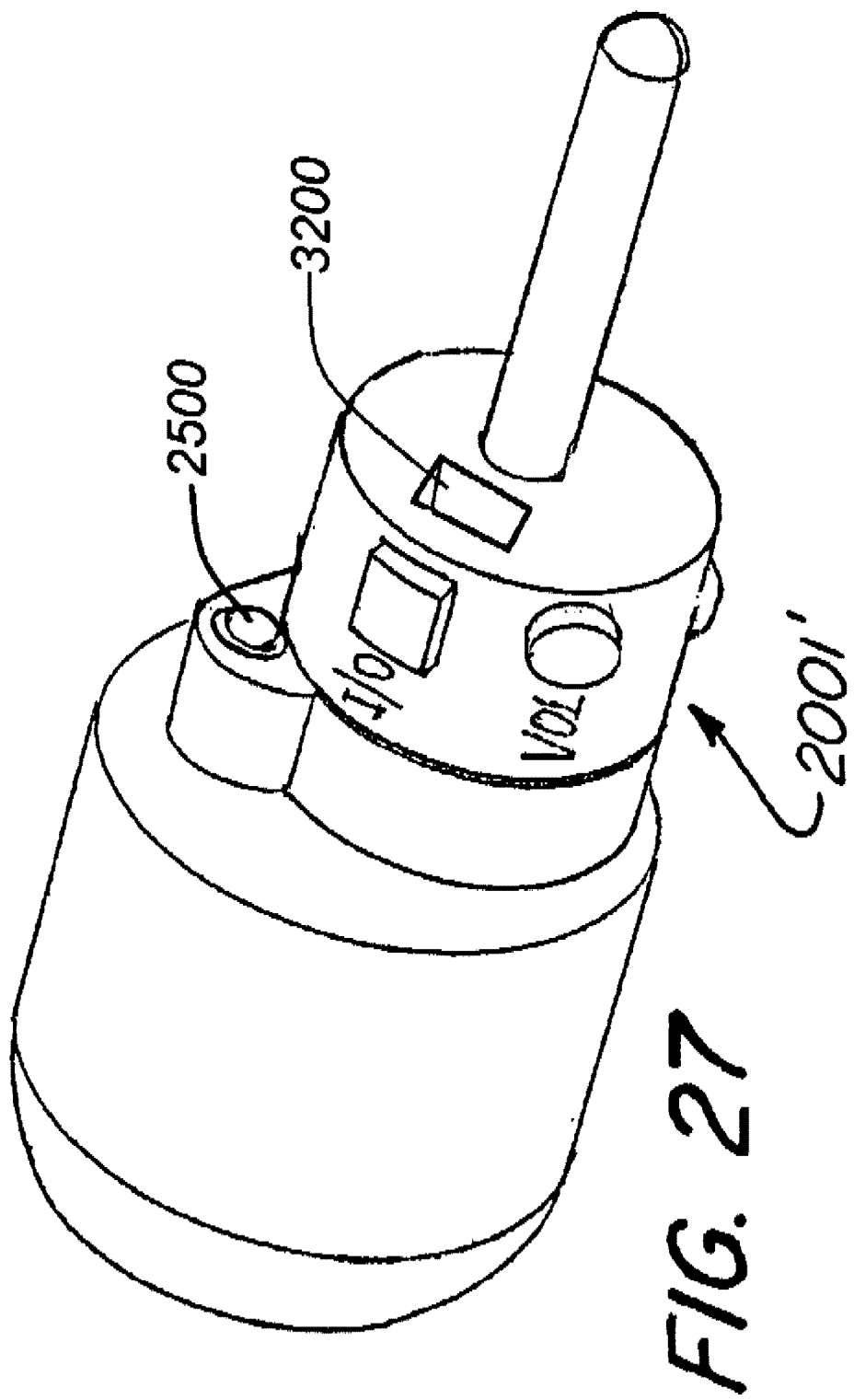
FIG. 27 is a perspective view of a third embodiment of the VSA and a hearing device combination.

FIG. 27 shows another embodiment where the amplifier, microphone and other electronics of the hearing aid/tinnitus device are configured so that the VSA/hearing aid or tinnitus device combination is an in the ear device. It is further understood that the earpiece may be more similar to the one shown in FIG. 11, such that it is molded to the shape of the user's ear. A microphone 2500 collects sound and amplifies it and delivers it to the end of the hearing aid fitted into the ear. The VSA has a similar structure as described above and in connection with FIG. 28 and allows selective control of the degree of ambient environmental sound.

It should be understood that FIGS. 20-27 also could be configured to use tinnitus devices with the VSA. Tinnitus devices typically would not have microphones 2500, but would still include the amplifier and speakers. These tinnitus devices commonly supply "white noise" into the ear of the wearer to mask what is often referred to as "ringing" in the ears. It is also understood that the term hearing aid as used herein could include a device that is a combination of a hearing aid and tinnitus device—that is that the device supplies amplified sound from a microphone and also white noise (which is another form of amplified sound). The white noise may be supplied at the same time as the amplified microphone sounds or may be supplied such that either amplified sound from the microphone or white noise (but not both) are transmitted into the user's ear.

Figure 28:
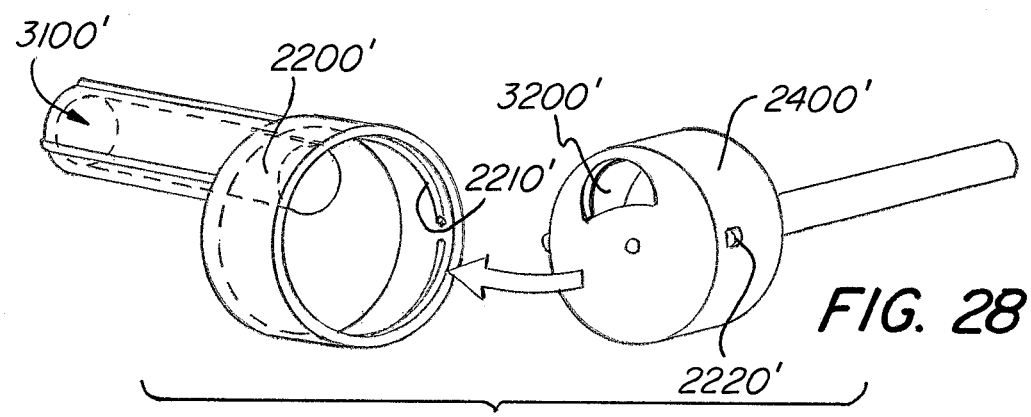
FIG. 28 is a perspective exploded view of an embodiment of the VSA of the invention, in which the hearing device is omitted.

FIG. 28 shows a VSA similar to the one shown in FIGS. 20-27, however the VSA in FIG. 28 does not have the passageway 3000 that connects to the hearing aid/tinnitus device. Second housing 2400' fits into first housing 2200'. Stop 2220' fits into channel 2210' so that passageway 3100' and 3200' can be rotated in and out of alignment to vary the amount of environmental sound passing through the VSA.

While the invention has been specifically described in connection with certain specific embodiments thereof, it is to be understood that this is by way of illustration and not of limitation and that various changes and modifications in form and details may be made thereto, and the scope of the appended claims should be construed as broadly as the prior art will permit.

While the invention has been specifically described in connection with certain specific application other applications of a user variable control over the environmental sound are not excluded. For example, use of a user's variable control level of an external environmental sound in such devices as headphones, earbuds or other listening devices is considered. This will allow the user to adjust the ratio between the sound being received via the primary source (MP3, DVD, radio, etc) and the sound present in the environment. The VSA would, therefore, serve as a passive, variable "noise cancelling/attenuation" device.

In another application, the VSA can be also used in any sound monitoring devices where there is a need to be also aware of some of the environmental sounds. For example, sport monitoring events, TV anchors, musicians etc.

Yet another application is in the field of hearing aids and tinnitus devices where there is a need to reduce or increase the amount of unamplified environmental sound. The VSA allows for a user's controlling such amount of unamplified sound.

In yet another embodiments, the VSA AC variable core can be inserted into a headphone/muffs type of ear attenuators.

It is understood that although some specific embodiments are described with respect to a hearing aid and/or tinnitus devices, other hearing devices may be substituted.

The description of the invention is merely exemplary in nature, and thus, variations that do not depart from the gist of the invention are intended to be within the scope of the invention. Such variations are not to be regarded as a departure from the spirit and scope of the invention.

Where a range of values is provided in this specification, each value between the upper and lower limits of that range is also specifically disclosed. The upper and lower limits of these smaller ranges may independently be included or excluded in the range as well. Additionally, although specific numbers may be quoted in the claims, it is intended that a number close to the one stated is also within the intended scope, such that the stated number is construed to mean "about." As used in this specification, the singular forms "a," "an," and "the" include plural referents unless the context clearly dictates otherwise. Additionally, if words are used to described how one component is disposed relative to another such as "circumferential," "radial," linearly," "orthogonal," and "perpendicular," the intended meaning is "substantially" "circumferential," "radial," linearly," "orthogonal," and "perpendicular." Further, it is intended that the specification and examples be considered as exemplary in nature and that variations that do not depart from the essence of the invention are intended to be within the scope of the invention. The references cited in this disclosure provide general background about the technology or components that can be incorporated into devices, systems and methods of the invention, each being relied on for purposes of providing a detailed disclosure of the invention and each incorporated by reference herein in its entirety.

What is claimed is:

1. A variable control sound attenuator and hearing aid or tinnitus device, comprising:
    a housing having a first housing and a second housing, the first housing being rotatable relative to and engaged with the second housing;
    the first housing being hollow and cylindrical and containing a first housing passageway therein, said first housing passageway extending through said first housing;
    the second housing being hollow and cylindrical and containing a second housing passageway therein, said second housing passageway extending through said second housing;
    rotation of the first housing providing a variable alignment between the first housing passageway and the second housing passageway thereby providing a variable control of sound transmission through the sound attenuator, wherein the rotation to align the first housing passageway and the second housing passageway provides an open passageway permitting sound transmission therethrough, and further the rotation to not align the first housing passageway and the second housing passageway provides a closed passageway blocking sound transmission therethrough; and
    a sound-amplifying hearing aid or a sound-generating tinnitus device.

2. The device of claim 1 wherein the rotation adjusts a mixture of environmental sound and sound from the hearing aid or tinnitus device.

3. The device of claim 1, further comprising an earpiece having an opening therethrough, the earpiece extending from the second housing and being radially offset from the center of the second housing, and the opening connecting with the second housing passageway;
    wherein the hearing aid or the tinnitus device is connected to the variable control sound attenuator and is configured to transmit sound through the opening of the earpiece.

4. The device of claim 3, further comprising a soft tip surrounding the earpiece.

5. The device of claim 1, wherein the first housing passageway is semi-cylindrical.

6. The device of claim 1, further comprising an element provided on the first housing which is stopped by stops on the second housing to limit rotation of the first housing on the second housing.

7. The device of claim 1, further comprising a motor engaged with the first housing to rotate the first housing and control the alignment between the first housing passageway and the second housing passageway.

8. The device of claim 7, wherein the housing has a ribbed upper portion and the motor is provided with a gear which is engaged with the ribbed upper portion to turn the housing radially to control the alignment between the first housing passageway and the second housing passageway.

9. The device of claim 8, further comprising an input device, the input device being able to actuate the motor.

10. The device of claim 1, further comprising a sound attenuating material in the first housing, with the first housing passageway extending therethrough.

11. The device of claim 1, further comprising a sound attenuating material in the second housing, with the second housing passageway extending therethrough.

12. The device of claim 1, wherein said first housing passageway is radially offset from the center of the first housing and wherein said second housing passageway is radially offset from the center of the second housing.

13. The device of claim 1 wherein said hearing aid or tinnitus device is a hearing aid and the hearing aid further comprises:
    a microphone which captures sound with greater emphasis from a direction transverse to the second passageway.

14. A variable control sound attenuator and hearing device configured to be worn by a user, comprising:
    a housing;
    a first passageway in said housing;
    a hearing aid having a forward-facing unidirectional microphone, the microphone being positioned to pick up sound from a direction transverse to the first passageway and to provide amplified sound;
    a second passageway in said housing and configured to connect to the hearing aid to deliver amplified sound;
    an adjustor connected to said housing and operable to move between open and closed positions to change an amount of environmental sound passing through the first passageway.

15. The device of claim 14 further comprising:
    an earpiece having at least one opening, the earpiece connected to the first and second passageways at the opening such that sound passes through the at least one opening.

16. The device of claim 14 wherein the adjustor modifies a size of an aperture through the first passageway between open and closed positions of the adjustor such that the adjustor adjusts a mixture between:
    the environmental sound passing through the first passageway; and
    the amplified sound from the hearing device.

17. The device of claim 14 wherein the sound amplification device includes a speaker positioned in said second passageway.

18. A hearing aid device having a variable control sound attenuator and configured to be at least partially placed in an ear of a wearer, comprising:
- a housing;
- a passageway in said housing;
- an earpiece;
- a sound-receiving microphone;
- a sound amplification device amplifying sound received in said microphone and providing amplified sound into said earpiece, wherein said microphone is directional and sound from a direction transverse to the first passageway is received by said microphone and amplified by the sound amplification device; and
- an adjustor operable to move between open and closed positions to thereby adjust a size of an aperture of the first passageway to change a mixture of sound passing into said earpiece, the mixture of sound between environmental sound through said passageway and the amplified sound.

19. The device of claim 18 wherein said earpiece is part of said housing.

20. The device of claim 18 wherein the sound amplification device includes a speaker, the speaker positioned in said housing.

21. The device of claim 20 wherein the sound amplification device transmits sound into said earpiece via a second passageway in said housing.

* * * * *